(12) United States Patent
Hara et al.

(10) Patent No.: US 7,344,874 B2
(45) Date of Patent: Mar. 18, 2008

(54) L-GLUTAMIC ACID-PRODUCING MICROORGANISM AND A METHOD FOR PRODUCING L-GLUTAMIC ACID

(75) Inventors: Yoshihiko Hara, Kawasaki (JP); Hiroshi Izui, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/070,085

(22) Filed: Mar. 3, 2005

(65) Prior Publication Data

US 2005/0196846 A1    Sep. 8, 2005

(30) Foreign Application Priority Data

Mar. 4, 2004    (JP) .............................. 2004-060542

(51) Int. Cl.
*C12N 1/20*    (2006.01)
*C12P 13/14*    (2006.01)

(52) U.S. Cl. .............................. 435/252.3; 435/252.32; 435/252.33; 435/110

(58) Field of Classification Search ............ 435/252.3, 435/252.33, 252.32, 110
See application file for complete search history.

(56) References Cited

U.S. PATENT DOCUMENTS

| | | | |
|---|---|---|---|
| 5,378,616 A | 1/1995 | Tujimoto et al. | |
| 5,393,671 A | 2/1995 | Tujimoto et al. | |
| 6,110,714 A | 8/2000 | Matsui et al. | |
| 6,331,419 B1 | 12/2001 | Moriya et al. | |
| 6,610,836 B1* | 8/2003 | Breton et al. ............... | 536/23.1 |
| 2002/0004231 A1 | 1/2002 | Moriya et al. | |
| 2002/0160461 A1 | 10/2002 | Nakai et al. | |
| 2002/0182688 A1 | 12/2002 | Izui et al. | |
| 2002/0192772 A1 | 12/2002 | Sato et al. | |
| 2003/0077764 A1 | 4/2003 | Tsujimoto et al. | |
| 2003/0190713 A1 | 10/2003 | Ueda et al. | |
| 2004/0029129 A1* | 2/2004 | Wang et al. ................... | 435/6 |
| 2004/0121428 A1 | 6/2004 | Sugimoto et al. | |

FOREIGN PATENT DOCUMENTS

| | | |
|---|---|---|
| EP | 0 670 70 | 9/1995 |
| EP | 0 952 221 | 10/1999 |
| EP | 0 955 368 | 11/1999 |
| EP | 0 999 282 | 5/2000 |
| EP | 1 078 989 | 2/2001 |
| WO | 97/23597 | 7/1997 |

OTHER PUBLICATIONS

Sequence alignment of WO200277183, Oct. 2002 only.*
Hoisehen, C., et al., "Evidence for an efflux carrier system involved in the secretion of glutamate by *Corynebacterium glutamicum*," Arch. Microbiol. 1989;151:342-347.
Database UniProt, Mar. 1, 2002, No. Q8X865.
Database UniProt, Nov. 1, 1995, No. P45537.
Database UniProt, Mar. 1, 2002, No. 08ZLK8.
Database EMBL, Oct. 29, 2001, No. AE008859.
Copy of International Search Report for PCT Appl. No. PCT/JP2005/004276 (Jun. 24, 2005).
International Preliminary Report on Patentability for PCT App. No. PCT/JP2005/004276 (Sep. 14, 2006).
Blattner, F. R., et al., "The Complete Genome Sequence of *Escherichia coli* K-12," Science 1997;277:1453-1462.
Harley, K. T., et al., "A Novel Ubiquitous Family of Putative Efflux Transporters," J. Mol. Microbiol. Biotechnol. 2000;2(2):195-198.
yhfK Genbank, Locus: NP_417817; Definition: putative dienelactone hydrolase [*Escherichia coli* K 12]; Accession No.: NP 417817; Version: NP 417817.1, GI: 16131237. 2 pp.

* cited by examiner

*Primary Examiner*—Maryam Monshipouri
(74) *Attorney, Agent, or Firm*—Shelly Guest Cermak; Cermak Kenealy & Vaidya LLP

(57) ABSTRACT

L-Glutamic acid is produced by culturing a microorganism in which an expression of L-glutamic acid-export gene, a yhfK gene, is enhanced or overexpressed, in a medium to produce and cause accumulation of L-glutamic acid in the medium, and collecting L-glutamic acid from the medium.

24 Claims, 4 Drawing Sheets

US 7,344,874 B2

L-GLUTAMIC ACID-PRODUCING MICROORGANISM AND A METHOD FOR PRODUCING L-GLUTAMIC ACID

This application claims priority to Japanese application 2004-060542, filed Mar. 4, 2004.

BACKGROUD OF THE INVENTION

1. Technical Field

The present invention relates to a method for producing L-glutamic acid. L-glutamic acid is widely used as a raw material for seasonings and so forth.

2. Background Art

L-Glutamic acid is primarily produced by fermentation utilizing L-glutamic acid-producing bacteria, including coryneform bacteria belonging to the genus *Brevibacterium*, *Corynebacterium* or *Microbacterium*, or mutant strains thereof (Kunihiko Akashi et al., Amino Acid Fermentation, Japan Scientific Societies Press [Gakkai Shuppan Center], pp. 195-215, 1986). Methods for producing L-glutamic acid by fermentation using other microorganisms have also been reported and methods for producing L-glutamic acid using a microorganism belonging to the genus *Bacillus, Streptomyces, Penicillium* or the like have been reported in U.S. Pat. No. 3,220,929. Methods for producing L-glutamic acid using a microorganism belonging to the genus *Pseudomonas, Arthrobacter, Serratia, Candida*, or the like have been reported in U.S. Pat. No. 3,563,857. Methods for producing L-glutamic acid using a microorganism belonging to the genus *Bacillus, Pseudomonas, Serratia, Aerobacter aerogenes* (currently referred to as *Enterobacter aerogenes*), or the like have been reported in JP32-9393B. Methods for producing L-glutamic acid using a mutant strain of *Escherichia coli* have been reported in JP5-244970A. In addition, methods for producing L-glutamic acid using a microorganism belonging to the genus *Klebsiella, Erwinia, Pantoea*, or *Enterobacter* have been reported in U.S. Pat. No. 6,197,559, U.S. Pat. No. 6,331,419 and European Patent Publication No.0999282).

Furthermore, methods for enhancing the activities of L-glutamic acid biosynthetic enzymes using recombinant DNA techniques to increase L-glutamic acid-producing ability have been disclosed. For example, it has been reported that the L-glutamic acid-producing ability of *Corynebacterium* or *Brevibacterium* bacteria (JP7-121228B) could be effectively improved by introducing a gene encoding citrate synthase derived from *Escherichia coli* or *Corynebacterium glutamicum*. Furthermore, it has also been reported that the L-glutamic acid-producing ability of enterobacteria belonging to the genus *Enterobacter, Klebsiella, Serratia, Erwinia*, or *Escherichia* (European Patent Publication No.0999282) could be effectively improved by introducing a citrate synthase gene derived from a coryneform bacterium.

Methods of improving the abilities of bacteria to produce substances such as amino acids by modifying an uptake or export system of the substances are known. As a method of modifying an uptake system for a substance, for example, a method of eliminating or reducing cellular uptake of a substance is known. Specifically, improving an L-glutamic acid-producing ability by eliminating or reducing cellular uptake of L-glutamic acid by deleting the gluABCD operon or a part thereof (European Patent Publication No. 1038970), or by reducing cellular uptake of the purine nucleotide for enhancing a purine nucleotide-producing ability (European Patent Publication No. 1004663), and so forth are known.

Methods for modifying an export system include enhancing an export system of an target substance and eliminating or reducing an export system of an intermediate or a substrate in a biosynthesis system of a target substance. For example, a method of producing L-lysine by utilizing a *Corynebacterium* bacterium strain in which expression of the L-lysine export gene (lysE) is enhanced have been reported (WO97/23597). Furthermore, a method of producing an L-amino acid using a microorganism in which expression of the rhtA, B, and C genes are enhanced has also been reported (European Patent Publication No.1013765). These genes have been reported to be involved in the export of L-amino acids. As a method of eliminating an export system of an intermediate or a substrate in a biosynthesis system of L-glutamic acid, mutating or disrupting a 2-oxoglutarate permease gene to reduce 2-oxoglutarate export, which is an intermediate of L-glutamic acid biosynthesis, is known (WO97/23597).

Furthermore, a method of breeding microorganisms has been suggested (WO00/37647) in which amino acid transport via the cell membrane is modified using a gene encoding the ATP binding cassette superfamily (ABC transporter), which is involved in the permeation of substances via a cell membrane.

In coryneform bacteria, it has been reported that addition of biotin or a surfactant changes the permeability of cell membranes, and thereby L-glutamic acid is exported from inside of the cells, which suggests that the export of L-glutamic acid in coryneform bacteria is not mediated by any export gene (Eiichiro Kimura, Metabolic Engineering of Glutamate Production, Advanced Biochemical Engineering Biotechnology, 79:37-57, 2003, Springer Verlag). Furthermore, it has also been reported that L-glutamic acid production efficiency was improved in *Escherichia* bacteria by enhancing the expression of a yfiK gene, which is thought to be involved in L-amino acid export (European Patent Publication 1016710).

However, an L-glutamic acid export gene has not been reported for a *Pantoea* microorganism or other microorganisms, and discovery of a novel L-glutamic acid export gene is desired.

Alternatively, a method of culturing a microorganism to produce and precipitate L-glutamic acid under acidic conditions is known (European Patent Publication 1078989). *Enterobacter* bacteria in which 2-oxoglutarate dehydrogenase activity is eliminated or reduced are often used in the fermentative production of precipitation of L-glutamic acid (European Patent Publication 1078989). In general, L-glutamic acid is converted into a TCA cycle intermediate, 2-oxoglutarate, in one step by glutamate dehydrogenase after it is imported into cells, and therefore it is generally considered that L-glutamic acid which is imported into cells is easily metabolized. However, when a microorganism having inactivated or reduced 2-oxoglutarate dehydrogenase activity is cultured under conditions for L-glutamic acid precipitation, the ratio of free L-glutamic acid having no electric charge becomes high, and readily passes through cell membranes, resulting in an increase in the intracellular L-glutamic acid concentration, and thus a decrease in bacterial cell growth. In European Patent Publication 1078989, a 2-oxoglutarate dehydrogenase-deficient strain which can efficiently produce and precipitate L-glutamic acid was bred by mutation treatment and used for the production of L-glutamic acid. However, few strains have been reported other than the above strain which can produce L-glutamic acid while also precipitating it, and no gene has been reported that can impart to a host microorganism L-glutamic acid resistance and L-glutamic acid-producing ability under conditions for precipitating L-glutamic acid.

The yhfK gene is a gene which exists on the genome of *Escherichia coli* (Science, 277(5331):1453-74, 1997), and it has been reported that it encodes a putative transporter based on the motifs, topology etc. of the predicted amino acid sequence (J. Mol. Microbiol. Biotechnol., 2 (2):195-198, 2000). However, neither cloning nor expression analysis of the gene has been previously reported. Furthermore, the actual function of the gene remains unknown.

SUMMARY OF THE INVENTION

An object of the present invention is to provide a microorganism that can efficiently produce L-glutamic acid and to also provide a method for efficiently producing L-glutamic acid using such a strain.

The inventors of the present invention conducted extensive research in order to achieve the aforementioned object, and as a result, they obtained the L-glutamic acid export gene yhfK which also confers L-glutamic acid-resistance. They also found that intracellular L-glutamic acid concentration was reduced in a strain in which the expression of the yhfK gene was enhanced, and the fermentation yield of L-glutamic acid was improved by using such a strain.

It is an object of the present invention to provide a microorganism having an ability to produce L-glutamic acid, wherein said microorganism is modified so that expression of a yhfK gene is enhanced.

It is a further object of the present invention to provide the microorganism as described above, wherein the expression of said yhfK gene has been enhanced by increasing a copy number of said yhfK gene or modifying an expression regulatory sequence of said yhfK gene.

It is a further object of the present invention to provide the microorganism as described above, wherein the amino acid sequence of a protein encoded by said yhfK gene is selected from the group consisting of SEQ ID NO: 10, 11 and 12, wherein said protein is able to export L-glutamic acid.

It is a further object of the present invention to provide the microorganism as described above, wherein said yhfK gene encodes a protein selected from the group consisting of:

(A) a protein comprising an amino acid sequence of SEQ ID NO: 2 or 4;

(B) a protein comprising an amino acid sequence of SEQ ID NO: 2 or 4, and wherein said protien includes substitution, deletion, insertion or addition of one or several amino acid residues, and wherein said protein is able to export L-glutamic acid.

It is a further object of the present invention to provide the microorganism as described above, wherein said yhfK gene encodes a protein comprising an amino acid sequence which is 70% or more homologous to the amino acid sequence of SEQ ID NO: 2 or 4, and wherein said protein is able to export L-glutamic acid.

It is a further object of the present invention to provide the microorganism as described above, wherein said yhfK gene is selected from the group consisting of:

(a) a DNA comprising a nucleotide sequence of numbers 1530 to 3620 in SEQ ID NO: 1 or numbers 201 to 2288 in SEQ ID NO: 3;

(b) a DNA which is able to hybridize to the nucleotide sequence of numbers 1530 to 3620 in SEQ ID NO: 1 or numbers 201 to 2288 in SEQ ID NO: 3, or a probe that is prepared from the nucleotide sequence under stringent conditions and encodes a protein which is able to export L-glutamic acid.

It is a further object of the present invention to provide the microorganism as described above, wherein said microorganism is a γ-proteobacterium.

It is a further object of the present invention to provide the microorganism as described above, wherein said microorganism is an Enterobacteriaceae selected from the group consisting of *Escherichia* bacterium, *Enterobacter* bacterium, *Pantoea* bacterium, *Klebsiella* bacterium, and *Serratia* bacterium.

It is a further object of the present invention to provide the microorganism as described above, wherein said microorganism is a *Coryneform* bacterium.

It is a further object of the present invention to provide a method for producing L-glutamic acid comprising culturing a microorganism as described above in a medium and collecting said L-glutamic acid from the medium.

It is a further object of the present invention to provide a gene encoding a protein selected from the group consisting of:

(A) a protein comprising an amino acid sequence of SEQ ID NO: 2; and (B) a protein comprising an amino acid sequence having 71% or more homology to the amino acid sequence of SEQ ID NO: 2, and wherein said protein is able to export L-glutamic acid.

It is further object of the present invention to provide a microorganism having an ability to produce L-glutamic acid, wherein said microorganism is modified to overexpress a yhfK gene.

It is further object of the present invention to provide the microorganism as described above, wherein said yhfK gene is overexpressed by increasing a copy number of said yhfK gene or by modifying an expression regulatory sequence of said yhfK gene.

Using the microorganism of the present invention, L-glutamic acid can be efficiently produced by fermentation. The gene of the present invention can be suitably used for breeding L-glutamic acid-producing microorganisms.

DETAILED DESCRIPTION OF THE PREFERRED EMBODIMENTS

Figure 1:
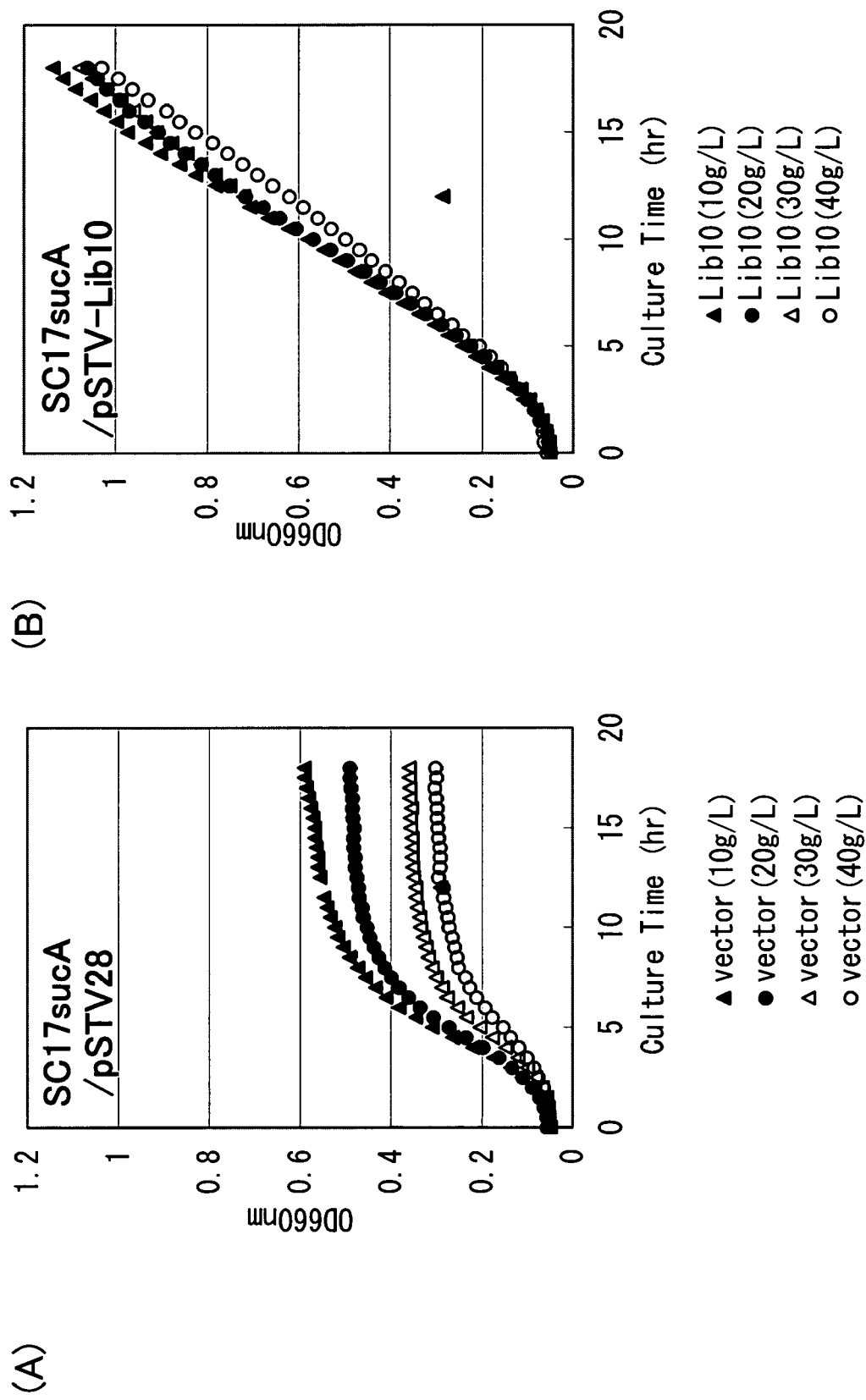
FIG. 1A-B show growth curves of a control *Pantoea ananatis* strain (A) and a *Pantoea ananatis* strain containing plasmid library (Lib10).

<1> L-Glutamic acid-producing microorganism of the present invention

The microorganism of the present invention has an ability to produce L-glutamic acid and has been modified so that expression of the yhfK gene is enhanced, or overexpressed. The term "ability to produce L-glutamic acid (L-glutamic acid-producing ability)" or "is able to produce L-glutamic acid" used herein means an ability to cause accumulation of L-glutamic acid in a medium or cells of the microorganism to such a degree that L-glutamic acid can be collected from the medium or cells when the microorganism of the present invention is cultured in the medium. The microorganism of the present invention may originally have the ability to produce L-glutamic acid, or may have obtained the ability to produce L-glutamic acid by modifying a parent strain such as those mentioned below by mutation or a recombinant DNA technique. Furthermore, a microorganism imparted with L-glutamic acid-producing ability by introduction or transformation of the yhfK gene of the present invention may be used.

Examples of a parent strain of the microorganism of the present invention which can be modified include those in the Enterobacteriaceae family classified as γ-proteobacteria such as the genus *Escherichia, Enterobacter, Pantoea, Kiebsiella, Serratia, Erwinia, Salmonella, Morganella*, or the like, coryneform bacteria belonging to the genus *Brevibacterium, Corynebacterium*, or *Microbacterium*, microorganisms belonging to the genus *Alicyclobacillus, Bacillus, Saceharomyces*, or the like, and so forth. Specifically, those belonging to "γ-proteobacteria" according to the classification provided by NCBI (National Center for Biotechnology Information) database can be used. In addition, methanol-assimilating bacteria such as *Methylophilus, Methylobacillus*, and so forth may also be used. These microorganisms can be cultured for production of L-amino acids in a medium containing methanol, which is a fermentation raw material available at low cost and in large amounts. These parent strains may or may not inherently possess the yhfK gene, but exhibit improved L-glutamic acid-export ability when the yhfK gene is introduced or transformed.

Examples of *Escherichia* bacteria include *Escherichia coli* and so forth. When an L-glutamic acid-producing strain of *Escherichia coli* is bred using a genetic engineering technique, the *E. coli* K12 strain and derivatives thereof, e.g., *Escherichia coli* MG1655 strain (ATCC No. 47076), W3110 strain (ATCC No. 27325) and so forth, can be utilized as a parent strain. The *Escherichia coli* K12 strain was isolated at Stanford University in 1922 and is a lysogenic bacterium of λ phage. In addition, it is a versatile strain having the F-factor, from which genetic recombinant strains can be created by conjugation or the like. Furthermore, the genomic sequence of *Escherichia coli* K12 strain has already been determined, and hence the gene information thereof is available. The *Escherichia coli* K12 strain and derivatives thereof can be obtained from the American Type Culture Collection (ATCC, Address: P.O. Box 1549, Manassas, Va. 20108, United States of America).

Furthermore, examples of *Enterobacter* bacteria include *Enterobacter agglomerans, Enterobacter aerogenes*, and so forth, and examples of *Pantoea* bacteria include *Pantoea ananatis*. Some strains of *Enterobacter agglomerans* recently were re-classified into *Pantoea agglomerans, Pantoea ananatis, Pantoea stewartii*, or the like on the basis of nucleotide sequence analysis of 16S rRNA etc. In the present invention, both the *Enterobacter* and *Pantoea* bacteria may be used so long as they are classified as γ-proteobacteria. When a *Pantoea ananatis* strain is bred by a genetic engineering technique, *Pantoea ananatis* AJ13355 strain (FERM BP-6614), AJ13356 strain (FERM BP-6615), AJ13601 strain (FERM BP-7207) and derivatives thereof may be used. These strains were identified as *Enterobacter agglomerans* when they were isolated and deposited as *Enterobacter agglomerans*. However, they were recently re-classified as *Pantoea ananatis* on the basis of nucleotide sequencing of 16S rRNA and so forth as described above.

The coryneform bacteria referred to herein are a group of microorganisms defined in Bergey's Manual of Determinative Bacteriology, 8th Ed., p. 599, 1974. They are aerobic, gram-positive, and nonacid-fast bacilli which are not able to sporulate, and include bacteria which have hitherto been classified into the genus *Brevibacterium* but united into the genus *Corynebacterium* at present (Int. J. Syst. Bacteriol., 41, 255, 1991), and also include bacteria belonging to the genus *Brevibacterium* or *Microbacterium*, which are closely related to the genus *Corynebacterium*.

Examples of coryneform bacteria suitable for L-glutamic acid production of the present invention are listed below.
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagens* (*Corynebacterium ammoniagens*)
*Brevibacterium album*
*Brevibacterium cerinum*
*Microbacterium ammoniaphilum*

Specifically, the following strains can be exemplified.
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* (*Corynebacterium glutamicum*) ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067
*Brevibacterium immariophilum* ATCC 14068
*Brevibacterium lactofermentum* (*Corynebacterium glutamicum*) ATCC 13665, ATCC 13869
*Brevibacterium roseum* ATCC 13825
*Brevibacterium saccharolyticum* ATCC 14066
*Brevibacterium thiogenitalis* ATCC 19240
*Brevibacterium ammoniagenes* (*Corynebacterium ammoniagens*) ATCC 6871
*Brevibacterium album* ATCC 15111
*Brevibacterium cerinum* ATCC 15112
*Microbacterium ammoniaphilum* ATCC 15354

Specific examples of *Methylophilus* bacteria include *Methylophilus methylotrophus*, and typical examples of *Methylophilus methylotrophus* include the AS1 strain (NCIMB 110515) and so forth. The *Methylophilus methylotrophus* AS1 strain (NCIMB 10515) is available from the National Collections of Industrial and Marine Bacteria (Address: NCIMB Lts., Torry Research Station, 135, Abbey Road, Aberdeen AB98DQ United Kingdom).

Specific examples of *Methylobacillus* bacteria include *Methylobacillus glycogenes*, *Methylobacillus flagellatum*, and so forth. Examples of *Methylobacillus glycogenes* include the T-11 strain (NCIMB 11375), ATCC 21276 strain, ATCC 21371 strain, ATR80 strain (described in Appl. Microbiol. Biotechnol., vol. 42, pp. 67-72, 1994), A513 strain (described in Appl. Microbiol. Biotechnol., vol. 42, pp. 67-72 (1994)), and so forth. The *Methylobacillus glycogenes* NCIMB 11375 strain can be provided from the National Collections of Industrial and Marine Bacteria (Address: NCIMB Lts., Torry Research Station 135, Abbey Road, Aberdeen AB98DG, United Kingdom). Examples of *Methylobacillus flagellatum* include the KT strain (Arch. Microbiol., vol. 149, pp. 441-446, 1988) and so forth.

<Imparting L-Glutamic Acid-Producing Ability>

Methods of imparting L-glutamic acid-producing ability to microorganisms as listed above include, for example, modifying the microorganisms so that expression of a gene encoding an enzyme involved in the L-glutamic acid biosynthesis is enhanced and/or overexpressed. Examples of enzymes involved in the L-glutamic acid biosynthesis include glutamate dehydrogenase (also referred to as "GDH" hereinafter), glutamine synthetase, glutamate synthase, isocitrate dehydrogenase, aconitate hydratase, citrate synthase (also referred to as "CS" hereinafter), phosphoenolpyruvate carboxylase (also referred to as "PEPC" hereinafter), pyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase, glucose phosphate isomerase, and so forth. Of these enzymes, it is preferable that the activity of one or more of CS, PEPC, and GDH is enhanced, and it is more preferable that activities of all three of these enzymes are enhanced.

Hereinafter, methods of modifying microorganisms so that expression of a target gene is enhanced will be explained.

One method is to increase the copy number of a target gene by cloning the target gene, inserting it into an appropriate plasmid, and transforming the host microorganism with the resulting plasmid. For example, the genes encoding CS (gltA gene), PEPC (ppc gene), and GDH (gdhA gene) from *Escherichia* and *Corynebacterium* bacteria have already been reported (Biochemistry, vol. 22, pp. 5243-5249, 1983; J. Biochem., vol. 95, pp. 909-916, 1984; Gene, vol. 27, pp. 193-199, 1984; Microbiology, vol. 140, pp. 1817-1828, 1994; Mol. Gen. Genet., vol. 218, pp. 330-339, 1989; Molecular Microbiology, vol. 6, pp. 317-326, 1992), and therefore these genes can be obtained by PCR using primers based on their nucleotide sequences from a chromosomal DNA from *Escherichia* or *Corynebacterium* bacteria.

Examples of plasmids which are autonomously replicable in microorganisms belonging to the family of Enterobacteriaceae and can be used for transformation include pUC19, pUC18, pBR322, RSF1010, pHSG299, pHSG298, pHSG399, pHSG398, pSTV28, pSTV29 (PHSG and pSTV can be obtained from Takara Bio), pMW119, pMW118, pMW219, pMW218 (plasmids of pMW series can be obtained from Nippon Gene), and so forth. Examples of plasmids for coryneform bacteria include pAM330 (JP58-67699A), pHM1519 (JP58-77895A), pAJ655, pAJ611, pAJ1844 (JP58-192900A), pCG1 (JP57-134500A), pCG2 (JP58-35197A), pCG4, pCG11 (JP57-183799A), pHK4 (JP5-7491A), and so forth. Phage DNAs may also be used as a vector instead of a plasmid. Examples of a plasmid which can be used for simultaneously enhancing the activities of CS, PEPC, and GDH include RSFCPG, which contains the gltA, ppc, and gdhA genes (EP 0952221A).

Specific examples of vectors that can replicate in *Methylobacillus* bacteria include RSF1010, which is a broad host spectrum vector, and derivatives thereof such as pAYC32 (Chistorerdov, A. Y., Tsygankov, Y. D. Plasmid, 16, 161-167, 1986), pMFY42 (Gene, 44, 53, 1990), pRP301, pTB70 (Nature, 287, 396, 1980), and so forth.

Examples of transformation methods include treating recipient cells with calcium chloride so as to increase permeability of the DNA, which has been reported for *Escherichia coli* K-12 (Mandel, M. and Higa, A., J. Mol. Biol., 53, 159 (1970)), preparing competent cells from cells which are at the growth phase, followed by transformation with DNA, which has been reported for *Bacillus subtilis* (Duncan, C. H., Wilson, G A. and Young, F. E., Gene, 1, 153 (1977)), and so forth. In addition to these methods, introducing a recombinant DNA into protoplast- or spheroplast-like recipient cells, which have been reported to be applicable to *Bacillus subtilis*, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, GR., Proc. Natl. Sci., USA, 75, 1929 (1978)), can be employed. In addition, transformation of microorganisms can also be performed by the electric pulse method (JP2-207791A).

A copy number of a gene can also be increased by integrating multiple copies of the gene into a chromosomal DNA of a microorganism. In order to integrate multiple copies of a gene into a chromosomal DNA of a microorganism, homologous recombination (Experiments in Molecular Genetics, Cold Spring Harbor Lab., 1972) can be carried out by targeting a sequence which exist in multiple copies on a chromosomal DNA. Repetitive DNA and inverted repeats at an end of a transposon can be used as a sequence which exists in multiple copies on a chromosomal DNA. Alternatively, as disclosed in EP0332488B, it is also possible to incorporate a target gene into a transposon, and allow it to be transferred so that multiple copies of the gene are integrated into the chromosomal DNA. Furthermore, a target gene can also be incorporated into a host chromosome by using Mu phage (EP0332488B).

Enhancing expression of a target gene can also be attained by replacing an expression regulatory sequence such as a promoter of the target gene on a chromosomal DNA or on a plasmid with a stronger one, as disclosed in WO00/18935. For example, lac promoter, trp promoter, trc promoter, and so forth are known as strong promoters. Moreover, it is also possible to introduce several nucleotide substitutions into a promoter region of a gene so that the promoter is more potent. Substitution of the expression regulatory sequence can be performed, for example, in the same manner as a gene substitution using a temperature-sensitive plasmid. Examples of a vector having a temperature-sensitive replication origin for *Escherichia coli* or *Pantoea ananatis* include plasmid pMAN997 described in WO99/03988 and so forth. Furthermore, substitution of an expression regulatory sequence can also be performed by using Red recombinase of λ phage (Datsenko, K. A., PNAS, 97(12), 6640-6645, 2000). Modification of an expression regulatory sequence can be combined with increasing a copy number of the gene.

Examples of microorganisms modified by the method as described above so that expression of the citrate synthase gene, phosphoenolpyruvate carboxylase gene and/or glutamate dehydrogenase gene are enhanced include the microorganisms disclosed in U.S. Pat. No. 6,197,559, U.S. Pat. No. 6,331,419, and European Patent Publication No.0999282 No.1078989.

The modification of a microorganism to impart L-glutamic acid-producing ability may be attained by enhancing 6-phosphogluconate dehydratase activity or 2-keto-3-deoxy-6-phosphogluconate aldolase activity. Examples of microorganisms modified so that expression of these genes are enhanced include microorganisms disclosed in European Patent Publication EP1352966.

The modification of a microorganism to impart L-glutamic acid-producing ability may be attained by reducing or inactivating the activity of an enzyme that catalyzes a reaction on a branch of the L-glutamic acid biosynthesis pathway, and producing a compound other than L-glutamic acid. Examples of enzymes catalyzing a reaction on a branch of the L-glutamic acid biosynthesis pathway and producing a compound other than L-glutamic acid include 2-oxoglutarate dehydrogenase, isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase, and so forth. Of these enzymes, it is preferable to reduce or eliminate the activity of 2-oxoglutarate dehydrogenase.

To reduce or inactivate the activities of the aforementioned enzymes, mutations for reducing or inactivating intracellular activities of the enzymes can be introduced by usual mutagenesis treatment methods or genetic engineering methods. Examples of mutagenesis treatment methods include irradiation by X-rays or ultraviolet rays, treament with a mutagenesis agent such as N-methyl-N'-nitro-N-nitrosoguanidine, and so forth. The mutation may be introduced into a coding region or an expression regulatory region such as a promoter. Examples of genetic engineering techniques include genetic recombination, transduction, cell fusion, and so forth.

Intracellular activity of the target enzyme and the degree of decrease in the activity can be confirmed by measuring the enzyme activity using a cell extract or a purified fraction thereof obtained from a candidate strain and comparing it with the activity of a wild-type or non-modified strain. For example, the 2-oxoglutarate dehydrogenase activity can be measured by the method of Reed et al. (Reed L. J. and Mukherjee B. B., Methods in Enzymology, 13, pp. 55-61, 1969).

Methods of inactivating or reducing the 2-oxoglutarate dehydrogenase activity in *Escherichia* bacteria are disclosed in U.S. Pat. No. 5,378,616, U.S. Pat. No. 5,573,945A, and so forth. A method of inactivating or reducing the 2-oxoglutarate dehydrogenase activity in coryneform bacteria is disclosed in WO95/34672. Furthermore, a method of inactivating or reducing the 2-oxoglutarate dehydrogenase activity in *Pantoea* bacteria is disclosed in JP2001-333769A.

Specific examples of bacteria having reduced or eliminated 2-oxoglutarate dehydrogenase activity include the following strains.

*Escherichia coli* AJ12624 (FERM BP-3853)
*Escherichia coli* AJ12628 (FERM BP-3854)
*Escherichia coli* AJ 12949 (FERM BP-4881)
*Brevibacterium lactofermentum* ΔS strain (WO95/34672).
*Pantoea ananatis* AJ13601 (FERM BP-7207 EP 1078989A)
*Pantoea ananatis* AJ13356 (FERM BP-6615 U.S. Pat. No. 6,331,419)
*Pantoea ananatis* SC17sucA (FERM BP-8646)
*Klebsiella platicola* AJ13410 (FERM BP-6617 U.S. Pat. No. 6,197,559)

The SC17sucA strain can be used to derive the AJ13601 strain (SC17sucA/RSFCPG+pSTVCB strain), and has a private number of AJ417 and was deposited at the National Institute of Bioscience and Human-Technology, Agency of Industrial Science and Technology, Ministry of Economy, Trade and Industry (1-1-3, Higashi, Tsukuba-shi, Ibaraki-ken, 305-8566) on Feb. 26, 2004 and given an accession number of FERM BP-08046.

Furthermore, the microorganism having L-glutamic acid-producing ability may constitutively express maleate synthase (aceB)•eisocitrate lyase (aceA)•isocitrate dehydrogenase kinase/phosphatase (aceK) operon (henceforth abbreviated as "ace operon"). Examples of microorganisms having such a property include the following.

*Escherichia coli* AJ 12628 (FERM BP-3854)
*Escherichia coli* AJ12624 (FERM BP-3853)

The former is a mutant strain having reduced 2-oxoglutarate dehydrogenase activity and constitutively expresses the ace operon, and the latter is a mutant strain in which 2-oxoglutarate dehydrogenase activity and L-glutamic acid decomposition activity is reduced (French Patent No. 2680178).

<Enhancing Expression of the yhfK Gene>

The microorganism of the present invention can be obtained by modifying a microorganism having L-glutamic acid-producing ability such as those mentioned above so that expression of the yhfK gene is enhanced. Alternatively, expression of the yhfK gene may be enhanced first, followed by imparting an L-glutamic acid-producing ability. Furthermore, the microorganism of the present invention may be a microorganism imparted with L-glutamic acid-producing ability by enhancing expression of the yhfK gene.

The expression of the yhfK gene may be enhanced by either enhancing the expression of the endogenous yhfK gene via modification of an expression regulatory sequence such as a promoter, or by exogenously introducing the yhfK gene using a plasmid or the like. These techniques may be combined.

Enhancing yhfK gene expression can be confirmed by measuring the amount of RNA transcribed from the yhfK gene in the bacterium of the present invention by northern hybridization or RT-PCR (Molecular cloning: Cold Spring Harbor Laboratory Press, Cold Spring Harbor (USA), 2001, and comparing it to that of a wild-type or non-modified strain. The expression of the yhfK gene in the microorganism of the present invention is enhanced more than that of a wild-type or non-modified strain, and preferably not less than 1.5-fold, more preferably not less than 2-fold, and most preferably not less than 3-fold of a wild-type or non-modified strain.

The "yhfK gene" used in the present invention includes genes derived from the Entrobacteriaceae family such as the yhfK gene from *Escherichia coil*, the yhfK gene from *Pantoea ananatis* or a homologue thereof. Examples of the yhfK gene from *Eseherichia coil* include a gene encoding a protein having the amino acid sequence of SEQ ID NO: 4, preferably a gene having the nucleotide sequence of the nucleotide numbers 201 to 2288 in SEQ ID NO: 3.

Examples of the yhfK gene derived from *Pantoea ananatis* include a gene encoding a protein having the amino acid sequence of SEQ ID NO: 2, preferably a gene having the nucleotide sequence of the nucleotide numbers 1530 to 3620 in SEQ ID NO: 1. yhfK gene may be the yhfK gene of *Shigella flexneri* represented by the nucleotide numbers 230947 to 233037 of GenBank Accession No. AE016992, and the yhfK gene of *Salmonella typhimurium* represented by the nucleotide numbers 4272 to 6359 of GenBank Accession No. AE008859. A homologue of *Eseherichia coli* or *Pantoea ananatis* yhfK gene refers to a gene which exhibits a high structural similarity to the both yhfK genes and enhances L-glutamic acid-export ability as well as L-glutamic acid-producing ability of the host microorganism. Examples of the yhfK gene homologue include a gene encoding a protein having an amino acid sequence of SEQ IDNOs: 10, 11, or 12. The amino acid sequence of SEQ ID NO: 10 is a sequence which is conserved between *Eseherichia coli* YhfK protein (SEQ ID NO: 4), YhfK protein of *Pantoea ananatis* (SEQ ID NO: 42), and YhfK homologues of *Shigella flexneri* and *Salmonella typhimurium*. The amino acid sequence of SEQ ID NO: 11 is a sequence which is conserved between *Eseherichia coli* YhfK protein and YhfK protein of *Salmonella typhimurium*. The amino acid sequence of SEQ ID NO: 12 is a sequence which is conserved between *Escherichia coli* YhfK protein and YhfK protein of *Salmonella enterica*_Paratyphi strain.

Furthermore, the yhfK gene may be cloned from a γ-proteobacterium such as *Enterobacter, Klebsiella, Serratia, Erwinia*, and *Yersinia* bacteria, a coryneform bacterium such as *Corynebacterium glutamicum* and *Brevibacterium lactofermentum, Pseudomonas* bacterium such as *Pseudomonas aeruginosa, Mycobacterium* bacterium such as *Mycobacterium tuberculosis* or the like, on the basis of homology to the genes exemplified above. The amino acid sequences of the proteins encoded by the yhfK genes of *Shigella flexneri* and *Salmonella typhimurium* have homologies of 99% and 86% to the amino acid sequence of SEQ ID NO: 4, respectively, and homologies of 70% and 71% to the amino acid sequence of SEQ ID NO: 2, respectively. The amino acid sequences of SEQ ID NOS: 2 and 4 have a homology of 70% to each other. The homology of amino acid sequence and DNA sequence can be determined using the algorithm BLAST (Proc. Natl. Acad. Sci. U.S.A., 90, and 5873 (1993)) and FASTA (Methods Enzymol., 183, and 63 (1990)) by Karlin and Altschul. The program called BLASTN and BLASTX is developed based on this algorithm BLAST.

The yhfK gene homologues include a gene derived from another microorganism, having high structural homology to the yhfK genes of *Escherichia coli* and *Pantoea ananatis* and having L-glutamic acid-export ability. The yhfK gene derived from another microorganism may be a gene encoding a protein having a homology of 70% or more, preferably 80% or more, more preferably 90% or more, particularly preferably 95% or more, to the total amino acid sequence of SEQ ID NO: 2 or 4, and having the ability to export L-glutamic acid.

The yhfK gene may encode a protein having an amino acid sequence of SEQ ID NO: 2 or 4, and include substitution, deletion, insertion or addition of one or several amino acid residues at one or more positions so long as the activity of the encoded protein, namely, L-glutamic acid-export ability, is maintained. Although the number of "several" amino acid residues referred to herein may differ depending on positions in the three-dimensional structure or types of amino acid residues of the protein, it may be preferably 2 to 20, more preferably 2 to 10, particularly preferably 2 to 5.

Such substitution of amino acids which contain functionally neutral sense mutations are conserved substitutions.

In the case of aromatic amino acids, conservative substitutions include when phe, trp, tyr replace each other. In the case of hydrophobic amino acids, conservative substitutions include when leu, ile, val replace each other. In the case of polar amino acids, conservative substitutions include when gin and asn substitute each other. In the case of basic amino acids, conservative substitutions include when arg, lys, his replace each other. In the case of acidic amino acids, conservative substitutions include when asp, and glu replace each other. In the case of hydroxyl group-containing amino acids, conservative substitutions include when ser and thr replace each other. Such substitution of amino acids is preferably a conserved substitution including substitution of ser or thr for ala, substitution of gin, his or lys for arg, substitution of glu, gin, lys, his or asp for asn, substitution of asn, glu or gin for asp, substitution of ser or ala for cys, substitution of asn, glu, lys, his, asp or arg for gin, substitution of gly, asn, gin, lys or asp for glu, substitution of pro for gly, substitution of asn, lys, gin, arg or tyr for his, substitution of leu, met, val or phe for ile, substitution of ile, met, val or phe for leu, substitution of asn, glu, gin, his or arg for lys, substitution of ile, leu, val or phe for met, substitution of trp, tyr, met, ile or leu for phe, substitution of thr or ala for ser, substitution of ser or ala for thr, substitution of phe or tyr for trp, substitution of his, phe or trp for tyr and substitution of met, ile or leu for val (ANTIMICROBIAL AGENTS AND CHEMTHERAPY, July, 2002 Vol46, No.7 p2208-2218).

Genes encoding the yhfK gene homologue can be obtained by modifying the nucleotide sequence shown in SEQ ID NO: 1 or 3, or SEQ ID Nos: 10, 11, 12, by, for example, site-specific mutagenesis, so that substitution, deletion, insertion or addition of an amino acid residue or residues is included at a specific site of the encoded protein. Furthermore, such a gene can also be obtained by a conventionally known mutation treatment. Examples of the mutation treatment include treating a gene having the nucleotide sequence shown in SEQ ID NO: 1 or 3 in vitro with hydroxylamine, and treating a microorganism, for example, an *Escherichia* bacterium, harboring the gene with ultraviolet ray irradiation or a mutagenesis agent used in a typical mutation treatments such as N-methyl-N'-nitro-N-nitrosoguanidine (NTG) or EMS (ethyl methanesulfonate). The mutation for the substitution, deletion, insertion, addition, inversion or the like of amino acid residues described above also includes a naturally occurring mutation arising from individual difference and difference in species of microorganisms harboring the yhfK gene (mutant or variant). Whether these genes encode a protein having L-glutamic acid-export ability can be confirmed by, for example, expressing the genes in a suitable cell and determining if the amount of the L-glutamic acid exported into the medium is increased.

The yhfK gene may also be a DNA hybridizable with a DNA having the nucleotide sequence of the numbers 1530 to 3620 in SEQ ID NO: 1, a DNA having the nucleotide sequence of the numbers 201 to 2288 in SEQ ID NO: 3 or a probe that can be prepared from these sequences under stringent conditions and encode a protein having L-glutamic acid-export ability.

"Stringent conditions" as used herein are conditions under which a so-called specific hybrid is formed, and a non-specific hybrid is not formed. Examples of stringent conditions include, those under which DNAs having high homology hybridize to each other, for example, DNAs having a homology of not less than 50%, hybridize to each other, and DNAs having homology lower than 50% do not hybridize to each other, and those under which DNAs hybridize to each other at a salt concentration with washing typical of Southern hybridization, i.e., washing once or preferably 2-3 times under 1×SSC, 0.1% SDS at 60° C., preferably 0.1×SSC, 0.1% SDS at 60° C., more preferably 0.1×SSC, 0.1% SDS at 68° C.

A partial sequence of the yhfK gene can also be used in the present invention. Such a probe can be prepared by PCR using oligonucleotides designed on the basis of the nucleotide sequence of the yhfK gene from a DNA fragment including the gene in a manner well known to those skilled in the art. When a DNA fragment having a length of about 300 bp is used as the probe, the washing conditions after hybridization can be exemplified by 2×SSC, 0.1% SDS at 50° C.

Enhancing the expression of the yhfK gene can be attained by increasing a copy number of the yhfK gene, modifying an expression regulatory sequence of the yhfK gene, amplifying a gene encoding a regulatory factor that increases expression of the yhfK gene, or disrupting or attenuating a gene encoding a regulatory factor that reduces expression of the yhfK gene, by using transformation or a homologous recombination technique.

For example, a recombinant DNA can be prepared by ligating a gene fragment containing the yhfK gene to a vector, preferably a multi-copy vector, which can replicate in the host microorganism, and introducing the resulting vector into the host microorganism.

The yhfK gene of *Escherichia coli* may be obtained by, for example, PCR (polymerase chain reaction, refer to White, T. J. et al., Trends Genet., 5, 185 (1989)) using primers based on the nucleotide sequence of SEQ ID NO: 3, for example, primers having a sequence of SEQ ID NO: 7 or 8, and using chromosomal DNA of *Escherichia coli* as a template. The yhfK gene of *Pantoea ananatis* may be obtained by, for example, PCR using primers based on a nucleotide sequence of SEQ ID NO: 1, for example, primers having a sequence of SEQ ID NO: 5 or 6, and using chromosomal DNA of *Pantoea ananatis* as a template. The yhfK gene from other microorganisms may also be used, and can be obtained from their chromosomal DNA or chromosomal DNA library by PCR using oligonucleotide primers based on a sequence of their yhfK gene or a homologous sequence thereof or the YhfK protein from a different species of microorganisms, or by hybridization using an oligonucleotide probe prepared based on such sequence information. A chromosomal DNA can be prepared from a microorganism serving as a DNA donor by, for example, the method of Saito and Miura (refer to H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992).

Then, a recombinant DNA is prepared by ligating the yhfK gene to a vector DNA replicable in the host microorganism. Preferably, vectors autonomously replicable in the host microorganism are used.

Examples of vectors autonomously replicable in *Escherichia coli* include pUC19, pUC18, pHSG299, pHSG399, pHSG398, pACYC184, (PHSG and pACYC are available from Takara Bio), RSF1010, pBR322, pMW219 (pMW is available from Nippon Gene), pTrc99A (Amann et al., Gene 69:301-315(1988), and so forth.

Examples of vectors which are autonomously replicable in Coryneform bacteria include pAM330 (JP58-67699A), pHM1519 (JP58-77895A), pVK7 (US2003-0175912), and pSFK6 (JP2000-262288A). Moreover, a shuttle vector autonomously replicable in both *Escherichia coli* and Coryneform bacteria may also be used.

Examples of vectors autonomously replicable in *Methylophilus* bacteria include RSF1010, and derivatives thereof such as pAYC32 (Chistorerdov, A. Y., Tsygankov, Y. D., Plasmid, 16, pp. 161-167 (1986)), pMFY42 (Gene, 44, p. 53 (1990)), pRK301, and pTB70 (Nature, 287, 396 (1980)).

In order to prepare a recombinant DNA by ligating the yhfK gene to any of the vectors mentioned above, the vector and a fragment containing the yhfK gene are digested with restriction enzymes and ligated to each other, usually by using a ligase such as a T4 DNA ligase.

To introduce a recombinant DNA prepared as described above into a microorganism, any known transformation method can be employed. These methods include treating recipient cells with calcium chloride so as to increase permeability of the DNA, using competent cells prepared from growing cells, introducing a recombinant DNA into protoplast- or spheroplast-like recipient cells, and the electric pulse method as described above.

The copy number of the yhfK gene can also be increased by integrating multiple copies of the gene into a chromosomal DNA of a microorganism. In order to integrate multiple copies of the yhfK gene into a chromosomal DNA of a microorganism, homologous recombination can be performed by targeting a sequence which exists in multiple copies on a chromosomal DNA. Repetitive DNA and inverted repeats at an end of a transposon can be used. Alternatively, as disclosed in JP2-109985A, it is also possible to incorporate the yhfK gene into a transposon, and allow it to be transferred so that multiple copies of the gene are integrated into the chromosomal DNA. Integration of the yhfK gene into the chromosome can be confirmed by southern hybridization using a probe having a partial sequence of the yhfK gene.

Enhancing expression of the yhfK gene can also be attained by replacing an expression regulatory sequence, including a promoter of the yhfK gene, on a chromosomal DNA or on a plasmid, with a stronger one, as described in WO00/18935. For example, the lac promoter, trp promoter, trc promoter, PL promoter, and so forth are known as strong promoters. Moreover, it is also possible to introduce several nucleotide substitutions into a promoter region for the yhfK gene so that the promoter is stronger. A method for evaluating strength of promoters and examples of strong promoters are disclosed in Goldstein et al. (Prokaryotic promoters in biotechnology. Biotechnol. Annu. Rev., 1995, 1, 105-128). Furthermore, it is known that a spacer sequence between the ribosome binding site (RBS) and translation initiation codon, especially, several nucleotides just upstream of the initiation codon, has a great influence on translation efficiency. Therefore, this sequence may be modified. Expression regulatory sequences of yhfK gene may be identified using a vector for promoter identification or genetic analysis software such as GENETYX. Expression is also improved by prolonging the lifetime of the mRNA. Furthermore, enzyme activity is also increased by preventing degradation of the enzyme protein.

The expression of the yhfK gene is enhanced by such substitution or modification of a promoter. The substitution of an expression regulatory sequence can also be attained by, for example, using a temperature-sensitive plasmid. Examples of a temperature-sensitive plasmid for Coryneform bacteria include p48K and pSFKT2 (JP2000-262288A), pHSC4 (refer to France Patent Laid-open Publication No. 2667875, 1992 and JP5-7491A), and so forth.

These plasmids can autonomously replicate at a temperature of at least 25° C., but cannot autonomously replicate at a temperature of 37° C. in Coryneform bacteria. Modifying the expression regulatory sequence may be combined with increasing the copy number of the yhfK gene.

In order to enhance an activity of the protein encoded by the yhfK gene, a mutation which increases an L-amino acid-export ability may be introduced into the yhfK gene. Examples of mutations that increase activity of the protein encoded by the yhfK gene (YhfK protein) include a promoter sequence mutation that increases the transcription of the yhfK gene and a yhfK gene coding region mutation that increases the specific activity of the YhfK protein.

The microorganism of the present invention is preferably one in which the L-glutamic acid-export ability is enhanced due to a modification which results in enhancing expression of the yhfK gene. The phrase "L-glutamic acid-export ability is enhanced" used herein means that when culturing a microorganism which has been modified to enhance expression of the yhfK gene, the amount of L-glutamic acid exported into the medium by the microorganism is more than that of an L-glutamic acid exported from a non-modified strain, such as a parent strain or a corresponding wild-type strain. The increase in L-glutamic acid-export ability is observed by determining the increase in concentration of the L-glutamic acid in the medium. Furthermore, the increase in L-glutamic acid-export ability is also observed by determining the decrease in intracellular concentration of the L-glutamic acid upon introduction of yhfK gene into a microorganism. The amount of L-glutamic acid exported from the microorganism of the present invention is preferably increased by 10% or more, more preferably 20% or more, particularly preferably 30% or more, when compared to the amount of L-glutamic acid exported from a non-modified strain. The absolute "L-glutamic acid-export ability" of a microorganism can be determined by measuring the difference between intracellular and extracellular concentrations of L-glutamic acid. Furthermore, the "L-glutamic acid-export ability" can also be determined indirectly by measuring cellular uptake of radiolabeled L-glutamic acid using everted membrane vesicles (J. Biol. Chem, vol. 277, No. 51, pp. 4984149849, 2002). For example, everted membrane vesicles are prepared from cells into which yhfK gene is introduced. Then, ATP or other substrates which provide driving energy are added to the vesicles, and cellular uptake of radiolabeled L-glutamic acid is measured. Alternatively, "L-glutamic acid-export ability" may be examined by measuring the rate of the exchange reaction between a non-labeled glutamic acid and a labeled glutamic acid in active cells.

The microorganism of the present invention may be a microorganism having an ability to cause accumulation of L-glutamic acid in a liquid medium at a concentration exceeding the saturation concentration of L-glutamic acid when it is cultured under acidic conditions (this ability is also referred to as the "L-glutamic acid accumulation ability under acidic conditions" hereinafter). Such a microorganism may be a microorganism that has come to have the L-glutamic acid accumulation ability under acidic conditions by enhancement of the expression of the yhfK gene, or a microorganism that originally has the L-glutamic acid accumulation ability under acidic conditions.

Examples of microorganisms originally having the L-glutamic acid accumulation ability under acidic conditions include the *Pantoea ananatis* AJ13355 strain (FERM BP-6614), AJ13356 strain (FERM BP-6615), AJ13601 strain (FERM BP-7207) (European Patent Publication 1078989), and so forth. The *Pantoea ananatis* AJ 13355 strain was deposited at the National Institute of Bioscience and Human-Technology, Agency of Industrial Science and Technology, Ministry of International Trade and Industry (currently, National Institute of Bioscience and Human-Technology, National Institute of Advanced Industrial Science and Technology; 1-3, Higashi 1-Chome, Tsukuba-shi, Ibaraki-ken, 305-8566, Japan) on Feb. 19, 1998 and given an accession number of FERM P-16644. The deposit was then converted to an international deposit under the provisions of Budapest Treaty on Jan. 11, 1999 and given an accession number of FERM BP-6614. This strain was identified as *Enterobacter agglomerans* when it was isolated and deposited as *Enterobacter agglomerans* AJ13355 strain. However, it was recently re-classified as *Pantoea ananatis* on the basis of nucleotide sequencing of 16S rRNA and so forth (refer to the examples described later). Although the AJ13356 and AJ13601 strains derived from the AJ13355 strain were also deposited at the aforementioned depository as *Enterobacter agglomerans*, they are similarly referred to as *Pantoea ananatis* in this description. The AJ13601 strain was deposited at the National Institute of Bioscience and Human-Technology, Agency of Industrial Science and Technology, Ministry of International Trade and Industry on Aug. 18, 1999 and given an accession number of FERM P-17516. The deposit was converted to an international deposit under the provisions of Budapest Treaty on Jul. 6, 2000 and given an accession number of FERM BP-7207.

<2> Method for Producing L-Glutamic Acid of the Present Invention

L-Glutamic acid can be produced by culturing the microorganism of the present invention in a medium to produce and cause accumulation of L-glutamic acid in the medium and collecting L-glutamic acid from the medium.

As the medium used for the culture, a conventional medium containing a carbon source, nitrogen source and inorganic salts as well as trace amount of organic nutrients such as amino acids and vitamins if required can be used. Either a synthetic or natural medium may be used. The carbon source and nitrogen source used in the medium may be of any type so long as they can be utilized by a strain to be cultured.

As the carbon source, saccharides such as glucose, glycerol, fructose, sucrose, maltose, mannose, galactose, starch hydrolysate, and molasses can be used. In addition, organic acids such as acetic acid and citric acid, or alcohols such as methanol and ethanol may be used either alone or in combination with another carbon source if a microorganism utilizing these carbon sources is used. As the nitrogen source, ammonia, ammonium salts such as ammonium sulfate, ammonium carbonate, ammonium chloride, ammonium phosphate and ammonium acetate, nitrate salts, and so forth can be used. As the trace amount of organic nutrients, amino acids, vitamins, fatty acids, nucleic acids, nutrients containing these substances such as peptone, casamino acid, yeast extract and soybean protein decomposition products can be used. When an auxotrophic mutant strain that requires an amino acid or the like for growth is used, the required nutrient is preferably supplemented. As mineral salts, phosphates, magnesium salts, calcium salts, iron salts, manganese salts, and so forth can be used.

The culture is performed under aerobic conditions. The culture temperature is preferably controlled at 20 to 45° C., and pH is preferably controlled at 3 to 9 during the culture. When pH decreases during the culture, the medium may be neutralized by the addition of, for example, calcium carbonate or an alkali such as ammonia gas. A substantial amount of L-glutamic acid accumulates in the culture broth after 10 to 120 hours of culture under conditions as described above.

Moreover, the culture may be performed under conditions which cause L-glutamic acid to precipitate. The conditions under which L-glutamic acid precipitates include acidic conditions, for example, conditions of pH 5.0 to 4.0, preferably pH 4.5 to 4.0, more preferably pH 4.3 to 4.0, particularly preferably pH 4.0.

After completion of the culture, L-glutamic acid can be collected from the culture broth by known collection methods. For example, the L-glutamic acid can be collected by concentrating the culture broth from which cells have been removed and crystallizing L-glutamic acid, or by isolating L-glutamic acid with ion exchange chromatography or the like. When the culture is performed under conditions which L-glutamic acid precipitates, the precipitate of L-glutamic acid in the medium can be collected by centrifugation, filtration or the like. In this case, it is also possible to further crystallize L-glutamic acid which is dissolved in the medium and then collect the L-glutamic acid.

EXAMPLES

Hereinafter, the present invention will be explained more specifically by referring to the non-limiting examples.

Example 1

<Screening of the L-Glutamic Acid-Export Gene>

Screening of the L-glutamic acid-export gene was performed as follows. Since L-glutamic acid is converted into an intermediate of the tricarboxylic acid cycle, 2-oxoglutarate, in one step by glutamate dehydrogenase, it is expected that L-glutamic acid flowing into cells under acidic conditions is easily metabolized in many microorganisms having glutamate dehydrogenase and the tricarboxylic acid cycle. Alternatively, a strain in which 2-oxoglutarate dehydrogenase gene is disrupted exhibits sensitivity to L-glutamic acid under acidic conditions. In this example, by using the *Pantoea ananatis* SC17sucA strain (JP2001-333769A) as a 2-oxoglutarate dehydrogenase-deficient strain, obtaining an L-glutamic acid-export gene based on L-glutamic acid-resistance under acidic conditions was attempted.

Chromosomal DNA was extracted from the *Pantoea ananatis* AJ13355 strain in a conventional manner, and partially digested with the restriction enzyme Sau3AI Then, a plasmid library was prepared by collecting and introducing fragments having a length of about 10 kb into the BamHI site of pSTV28 (Takara Bio). This plasmid library was introduced into the SC17sucA strain by electroporation in a conventional manner. The SC17sucA strain, a strain from which AJ13601 strain (SC17sucA/RSFCPG+pSTVCB strain) can be obtained, has a private number of AJ417 and was deposited at the National Institute of Bioscience and Human-Technology, Agency of Industrial Science and Technology, Ministry of Economy, Trade and Industry (1-1-3, Higashi, Tsukuba-shi, Ibaraki-ken, 305-8566) on Feb. 26, 2004 and given an accession number of FERM BP-08046.

The SC17sucA strain containing the plasmid library as described above was selected on a plate of L medium (medium containing 10 g of Bacto tryptone, 5 g of yeast extract, 5 g of NaCl and 15 g of agar per 1 L of pure water, pH 7.0) mixed with ingredients of minimal medium (0.5 g of glucose, 2 mM magnesium sulfate, 3 g of monopotassium phosphate, 0.5 g of sodium chloride, 1 g of ammonium chloride and 6 g of disodium phosphate per 1 L of pure water) on the basis of chloramphenicol-resistance, and $4.33 \times 10^5$ transformant colonies were obtained. These $4.33 \times 10^5$ transformants were plated on a minimal medium with an adjusted pH of 4.5. The transformants contain a high concentration of glutamic acid where the SC17sucA strain cannot form colonies. Specifically, the transformants were plated on a medium which comprises each component of the minimal medium, 30 g/L of L-glutamic acid, 100 mg/L each of lysine, methionine and diaminopimelic acid, and glucose and sucrose as carbon sources and is adjusted to pH 4.5.

The transformants were cultured at 34° C. for 3 days, and each gene inserted into the vector introduced into the cells contained in colonies was analyzed. Plasmids were extracted from each library and treated with restriction enzymes to confirm the sizes of the inserted gene. As a result, 15 clones out of 16 clones obtained from the minimal medium with sucrose as a carbon source showed the same pattern of restriction enzyme treatment. A plasmid exhibiting the same pattern of restriction enzyme treatment was also obtained from 11 clones which appeared on the minimal medium with glucose as a carbon source. The plasmid was designated plasmid library Lib10.

Then, a control SC17sucA strain and a SC17sucALib10 strain containing the plasmid library Lib10 were each cultured in a liquid medium prepared by adding 30 g/L of L-glutamic acid, 100 mg/L each of lysine, methionine and diaminopimelic acid to the minimal medium (medium containing 0.5 g of glucose or sucrose, 2 mM magnesium sulfate, 3 g of monopotassium phosphate, 0.5 g of sodium chloride, 1 g of ammonium chloride and 6 g of disodium phosphate in 1 L of pure water) and adjusted to pH 4.5. Growth of the strains on the minimal medium containing high concentrations of L-glutamic acid under acidic conditions was examined.

The results are shown in FIG. 1. Growth of the SC17sucALib10 strain containing the plasmid library Lib10 was found to markedly improve as compared to SC17sucA in the presence of high concentrations of L-glutamic acid under acidic conditions. Accordingly, it was determined that Lib10 contains a gene which confers L-glutamic acid-resistance under acidic conditions, and therefore it was decided to determine the nucleotide sequence of the gene contained in Lib10 and estimate the function of the protein encoded by the gene.

The nucleotide sequences were determined in a conventional manner and compared with genes registered at GenBank for homology. As a result, it was found that this region contains genes having homology to a part of yhfk (AE 000411.1:9304 . . . 11394) of *Escherichia coli* MG1655. But the function of yhfK is unknown.

Example 2

<Effect of yhfK Gene Amplification>

Because it was suggested that yhfK might encode a transporter on the basis of a search of protein motifs (J. Mol. Microbiol. Biotechnol., 2(2):195-198, 2000), it was decided to examine the effect of amplification of yhfK gene among the aforementioned genes.

The yhfK gene fragment was amplified by PCR using the oligonucleotides yhfK-F1 and yhfK-R2, which have nucleotide sequences shown in SEQ ID NOS: 5 and 6, respectively, and are from a chromosomal DNA of a wild-type strain of *Pantoea ananatis*, No.359 (AJ13355). pGEM-yhfK was prepared by ligating the obtained fragment to a TA-cloning vector, pGEM-Teasy (Promega). pGEM-yhfK was digested with EcoRI and ligated to EcoRI-digested pSTV28

Figure 2:
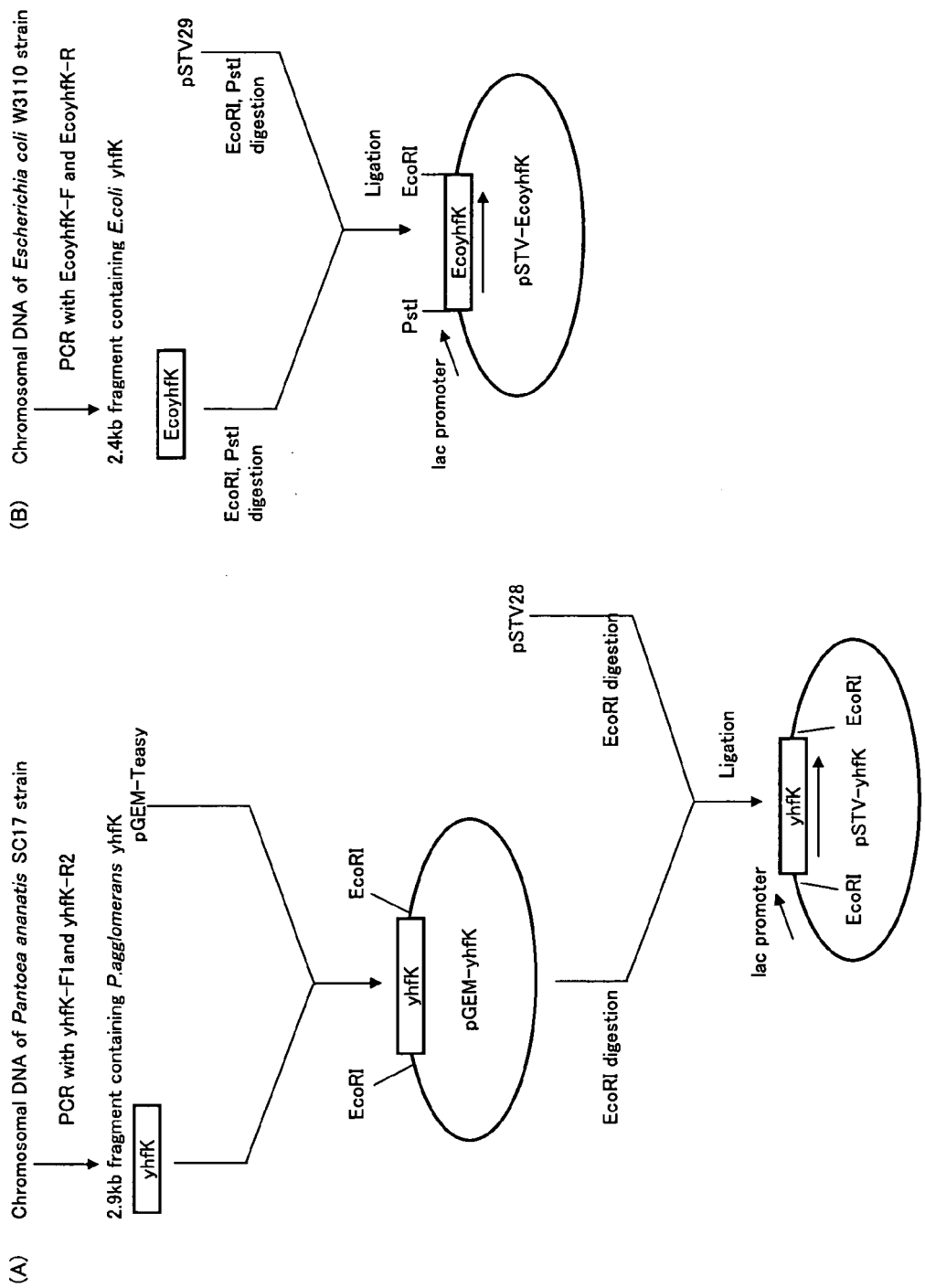
FIG. 2 shows construction procedures of a plasmid for amplification of the yhfK gene of *Pantoea ananatis*(A) and a plasmid for amplification of the yhfK gene of *Escherichia coli* (B).

(Takara Bio) to construct a vector pSTV-yhfK for yhfK gene amplification. The construction scheme of the plasmid is shown in FIG. 2.

The vector pSTV-yhfK for yhfK gene amplification and a control plasmid, pSTV28, were each introduced into the SC17sucA strain by electroporation, and transformants exhibiting chloramphenicol-resistance were selected. The obtained plasmids were isolated and the presence of pSTV-yhfK was confirmed. The yhfK-amplified strain was designated SC17sucA/pSTV-yhfK, and the control pSTV-introduced strain was designated SC17sucA/pSTV28.

SC17sucA and SC17sucA/pSTV-yhfK were plated on a medium prepared by adding 30 g/L of L-glutamic acid, 100 mg/L each of lysine, methionine and diaminopimelic acid to the minimal medium (medium containing 0.5 g of glucose or sucrose, 2 mM magnesium sulfate, 3 g of monopotassium phosphate, 0.5 g of sodium chloride, 1 g of ammonium chloride and 6 g of disodium phosphate in 1 L of pure water) and adjusted to pH 4.5 with aqueous ammonia, and the growth of these strains were analyzed. Whereas SC17sucA could not form colonies, SC17sucA/pSTV-yhfK formed colonies on the minimal medium which contained high concentrations of L-glutamic acid.

Figure 3:
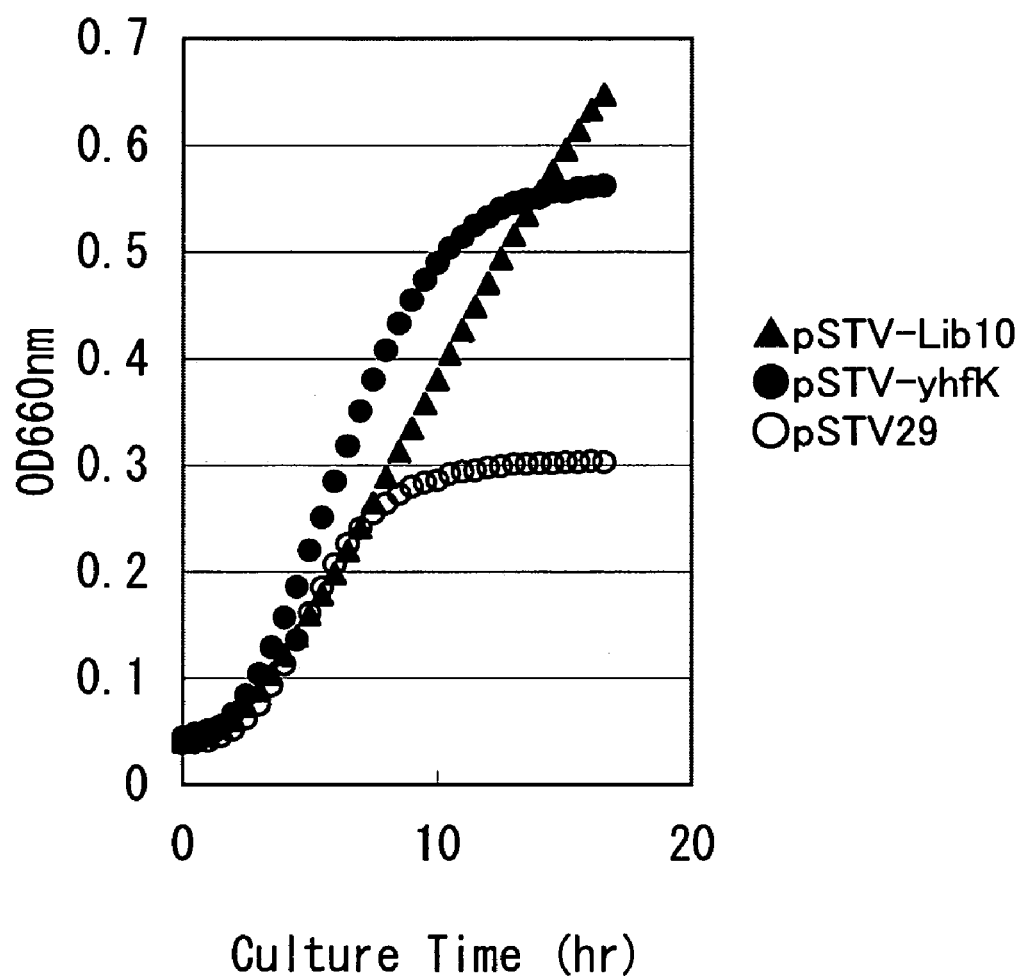
FIG. 3 shows growth curves of a control strain, a plasmid library (Lib10)-amplified strain, and yhfK-amplified strain of *Pantoea ananatis*.

Then, the strains were cultured in a liquid medium which was prepared by adding 30 g/L of L-glutamic acid, 100 mg/L each of L-lysine hydrochloride, DL-methionine and α-diaminopimelic acid to the minimal medium (medium containing 0.5 g of glucose or sucrose, 2 mM magnesium sulfate, 3 g of monopotassium phosphate, 0.5 g of sodium chloride, 1 g of ammonium chloride and 6 g of disodium phosphate in 1 L of pure water) and adjusting to pH 4.5 with aqueous ammonia. Growth in the minimal medium containing high concentrations of L-glutamic acid under acidic conditions was then examined. The results are shown in FIG. 3.

Growth of the SC17sucA/pSTV-yhfK strain improved as compared with the control SC17sucA/pSTV28 strain, as in the case where Lib10 was introduced, and therefore it was revealed that the yhfK gene imparted the phenotype of L-glutamic acid-resistance under acidic conditions as compared to the SC17sucA strain.

Example 3

<Effect of yhfK Gene Amplification on L-glutamic Acid Production at Neutral pH>

Then, in order to examine effect of this gene on L-glutamic acid production, the plasmid for yhfK amplification, pSTV-yhfK, was introduced into the L-glutamic acid-producing bacterium SC17sucA/RSFCPG which contains RSFCPG, a plasmid for L-glutamic acid production having a nucleotide sequence shown in SEQ ID NO: 9 (European Patent Publication 1078989).

The plasmid pSTV-yhfK and the control plasmid pSTV29 (Takara Bio) were each introduced into SC17sucA/RSFCPG by electroporation, and transformants were selected based on chloramphenicol-resistance. After confirming the presence of the plasmids, the strain containing the plasmid for yhfK amplification was designated SC17sucA/RSFCPG+pSTV-yhfK, and the control pSTV29-containing strain was designated SC17sucA/RSFCPG+pSTV29.

Then, the L-glutamic acid producing ability was examined by culturing the SC17sucA/RSFCPG+pSTV-yhfK and the control SC17sucA/RSFCPG+pSTV29. The composition of the medium is as follows.

[Composition of Culture Medium]

| | |
|---|---|
| Sucrose | 50 g/L |
| $MgSO_4 \cdot 7H_2O$ | 0.4 g/L |
| $KH_2PO_4$ | 2.0 g/L |
| Yeast extract | 4.0 g/L |
| $FeSO_4 \cdot 7H_2O$ | 0.01 g/L |
| $MnSO_4 \cdot 5H_2O$ | 0.01 g/L |
| L-Lysine hydrochloride | 0.4 g/L |
| DL-Methionine | 0.4 g/L |
| ε-Diaminopimelic acid | 0.4 g/L |
| Tetracycline hydrochloride | 25 mg/L |
| Chloramphenicol | 25 mg/L |

SC17sucA/RSFCPG+pSTV29 and SC17sucA/RSFCPG+pSTV-yhfK were precultured on the L medium (medium containing 10 g of Bacto tryptone, 5 g of yeast extract, 5 g of NaCl and 15 g of agar in 1 L of pure water, pH 7.0) mixed with ingredients of the minimal medium (medium containing 0.5 g of sucrose, 2 mM magnesium sulfate, 3 g of monopotassium phosphate, 0.5 g of sodium chloride, 1 g of ammonium chloride and 6 g of disodium phosphate in 1 L of pure water), 25 mg/L of chloramphenicol and 12.5 mg/L tetracycline, and the cells collected from one whole plate were inoculated in ajar fermenter and cultured at 34° C., pH 6.0 under aeration of 1/1 vvm with controlled stirring so that the oxygen concentration is 5% or more.

The results are shown in Table 1. It was found that L-glutamic acid accumulation caused by the yhfK-amplified strain, SC17sucA/RSFCPG+pSTV-yhfK, increased by about 3 g/L, i.e., about 5% in terms of the yield per sugar, as compared with SC17sucA/RSFCPG+pSTV29.

TABLE 1

Effect of yhfK gene amplification under neutral condition

| | OD 620 nm (×1/101) | L-glutamic acid (g/L) |
|---|---|---|
| SC17sucA/RSFCPG + pSTV29 | 0.381 | 22.6 |
| SC17sucA/RSFCPG + pSTV-yhfK | 0.351 | 25.4 |

Example 4

<Effect of Amplification of *Escherichia coli* yhfK Gene and L-glutamic Acid Production under Acidic Conditions>

Then, the yhfK gene of *Escherichia coli* was introduced into the *Pantoea ananatis* SC17sucA/RSFCPG strain, and the effect of the introduction was examined.

PCR was performed using the oligonucleotides having a nucleotide sequence shown in SEQ ID NOS: 7 and 8 designed on the basis of the sequence of yhfK of *Escherichia coli* registered at GeneBank as NC_000913 (SEQ ID NO: 3) and the chromosomal DNA of the *Escherichia coli* W3110 strain (ATCC 27325) was used as a template, and a fragment of about 2.4 kb containing the yhfK gene was obtained. This fragment was treated with EcoRI and PstI and ligated to pSTV29 (Takara Shuzo), which had been digested with the same restriction enzymes. The obtained plasmid for amplification of yhfK of *Escherichia coli* was designated plasmid pSTV-EcoyhfK. The construction scheme is shown in FIG. 2.

The obtained plasmid pSTV-EcoyhfK was introduced into the aforementioned SC17sucA/RSFCPG strain by electroporation, and transformants were selected based on chloramphenicol-resistance. The obtained *Escherichia coli* yhfK gene-amplified strain was designated SC17sucA/RSFCPG+pSTV-EcoyhfK.

Then, L-glutamic acid was produced using this strain. That is, SC17sucA/RSFCPG+pSTV-yhfK, SC17sucA/RSFCPG+pSTV-EcoyhfK and control SC17sucA/RSFCPG+pSTV29 strain were cultured, and the L-glutamic acid producing-ability thereof was examined. The culture was performed in two stages, i.e., seed culture for cell formation and main culture for L-glutamic acid production.

The seed culture was performed by using a medium having the following composition.

[Composition of Seed Culture Medium]

| Sucrose | 50 g/L |
| --- | --- |
| MgSO$_4$•7H$_2$O | 0.4 g/L |
| GD113 | 0.1 mL/L |
| (NH$_4$)$_2$SO$_4$ | 4 g/L |
| KH$_2$PO$_4$ | 2.0 g/L |
| Yeast extract | 4.0 g/L |
| FeSO$_4$•7H$_2$O | 0.01 g/L |
| MnSO$_4$•5H$_2$O | 0.01 g/L |
| L-Lysine hydrochloride | 0.4 g/L |
| DL-Methionine | 0.4 g/L |
| ε-Diaminopimelic acid | 0.4 g/L |
| Tetracycline hydrochloride | 12.5 mg/L |
| Chloramphenicol | 25 mg/L |

The SC17sucA/RSFCPG+pSTV29 strain, SC17sucA/RSFCPG+pSTV-yhfK strain, and SC17sucA/RSFCPG+pSTV-EcoyhfK strain were precultured on the L medium (medium containing 10 g of Bacto tryptone, 5 g of yeast extract, 5 g of NaCl and 15 g of agar in 1 L of pure water, pH 7.0) mixed with ingredients of minimal medium (medium containing 0.5 g of glucose, 2 mM magnesium sulfate, 3 g of monopotassium phosphate, 0.5 g of sodium chloride, 1 g of ammonium chloride and 6 g of disodium phosphate in 1 L of pure water), 25 mg/L of chloramphenicol and 12.5 mg/L of tetracycline, and the cells from one whole plate were inoculated in ajar fermenter for seed culture and cultured at 34° C., pH 6.0 for 14 hours under aeration of 1/1 vvm with controlled stirring so that the oxygen concentration is 5% or more. pH was controlled at 6.0 by the addition of ammonia gas during the culture. The seed culture was continued until the sugar was depleted in the medium. Then, the main culture was performed in a medium having the following composition.

[Composition of Main Culture Medium (Concentrations after 20% of Seed Culture Medium is Added)]

| Sucrose | 50 g/L |
| --- | --- |
| (NH$_4$)$_2$SO$_4$ | 5.0 g/L |
| MgSO$_4$•7H$_2$O | 0.4 g/L |
| GD113 | 0.1 mL/L |
| Yeast extract | 6.0 g/L |
| KH$_2$PO$_4$ | 6.0 g/L |
| NaCl | 1.5 g/L |
| FeSO$_4$•7H$_2$O | 0.02 g/L |
| MnSO$_4$•5H$_2$O | 0.02 g/L |
| L-Lysine hydrochloride | 0.8 g/L |
| DL-Methionine | 0.6 g/L |
| DL-α,ε-Diaminopimelic acid | 0.6 g/L |
| Tetracycline hydrochloride | 12.5 mg/L |
| Chloramphenicol | 25 mg/L |
| Calcium chloride dihydrate | 0.75 g/L |
| Calcium pantothenate | 12 mg/L (added only for culture with addition of pantothenic acid) |

The obtained cells in a volume of 60 mL were added into a 1-L volume mini jar containing 240 mL of the medium and cultured at pH 4.7. After 50 g/L of sucrose which was contained in the main culture medium was consumed, 700 g/L (w/v) of a sucrose solution (sterilized by autoclaving) was fed by a pump to control the sugar concentration in the small fermentation tank to 5 to 20 g/L.

The results are shown in Table 2. The main culture was terminated after the same culture duration for all of the strains. For both the SC17sucA/RSFCPG+pSTV-EcoyhfK strain in which yhfK gene of *Escherichia* bacterium was amplified, and the SC17sucA/RSFCPG+pSTV-yhfK strain in which yhfK gene of *Pantoea ananatis* was amplified, the yield of L-glutamic acid markedly increased, and the sugar consumption rate was higher as compared with those obtained with the control the SC17 sucA/RSFCPG+pSTV29 strain. Thus, it was found that the yhfK gene amplification exerted a growth improvement effect in L-glutamic acid production culture, in addition to an improvement effect on the yield of L-glutamic acid.

TABLE 2

Results for *Pantoea ananatis*-derived yhfK-amplified strain and *Escherichia coli*-derived yhfK-amplified strain under acidic condition (main culture)

| | SC17sucA/ RSFCPG + pSTV29 | SC17sucA/ RSFCPG + pSTV-yhfK | SC17sucA/ RSFCPG + pSTV-EcoyhfK |
| --- | --- | --- | --- |
| Accumulation of produced L-glutamic acid (g/L) | 46.0 | 100.0 | 76.0 |
| Culture time | 29.5 | 29.5 | 29.5 |

Example 5

<Evaluation of L-glutamic Acid-Export Ability of yhfK Gene>

The L-glutamic acid concentrations in the cells of the yhfK gene-amplified strains were measured. The intracellular concentration of L-glutamic acid was measured by referring to the method disclosed in A. Ishizaki et al., Biotech. Teqniq., vol. 9, No. 6, p. 409, 1995. The culture medium in a volume of 1 mL was added to 1.5-mL tube containing 500 μL of silicone oil and immediately centrifuged for 3 minutes at 15,000 rpm in a centrifugal machine. Then, the bottom of the tube was cut, and the cells were collected. The cells were put into a 2-mL tube containing 200 μL of 5N perchloric acid and stored at −80° C. before the measurement. This perchloric acid solution containing the cells was thawed at room temperature, suspended and neutralized by the addition of 200 μL of 2.5 M potassium carbonate. The precipitates were removed by centrifugation, and then L-glutamic acid concentration in the supernatant was measured as an intracellular concentration of L-glutamic acid.

Figure 4:
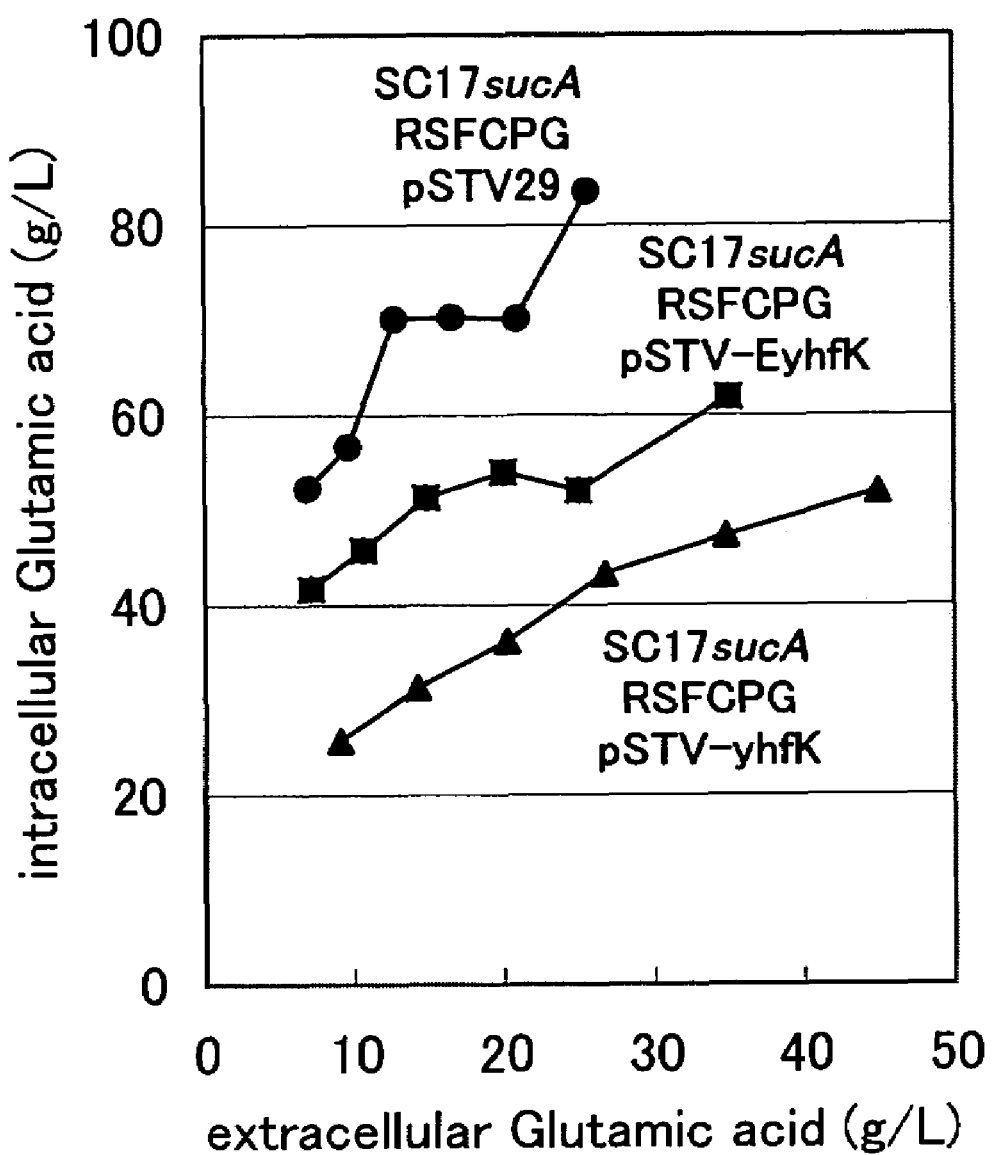
FIG. 4 shows a comparison of the ratio of intracellular and extracellular L-glutamic acid concentrations for strains an amplified yhfK gene derived from *Escherichia coli* or *Pantoea ananatis*.

The results are shown in FIG. 4. The horizontal axis indicates the extracellular L-glutamic acid concentration, and the vertical axis indicates the intracellular L-glutamic acid concentration. It was revealed that, whereas the intracellular L-glutamic acid concentration was higher than the extracellular L-glutamic acid concentration in the control SC17sucA/RSFCPG+pSTV29 strain, the intracellular L-glutamic acid concentration was lower than the extracellular L-glutamic acid concentration in the SC17sucA/RSFCPG+pSTV-EcoyhfK and SC17sucA/RSFCPG+pSTV-yhfK. These results indicate that the yhfK gene-amplified strains such as SC17sucA/RSFCPG+pSTV-EcoyhfK and SC17sucA/RSFCPG+pSTV-yhfK became more likely to export intracellular L-glutamic acid to outside of the cells. Therefore, it was found that yhfK gene is a gene encoding an L-glutamic acid-export protein which can export intracellular L-glutamic acid to the outside of the cells.

Example 6

<Evaluation of L-Glutamic Acid-Producing Ability of Escherichia coli in which the yhfK Gene is Amplified>

Then, the yhfK gene derived from Pantoea ananatis was introduced into Escherichia coli, and the effect of amplification of the gene was examined.

The aforementioned vector for amplification of the yhfK gene derived from Pantoea ananatis, pSTV-yhfK, and the control plasmid pSTV29 were each introduced into an Escherichia coli wild-type strain, W3110, by electroporation and transformants exhibiting chloramphenicol-resistance were selected. The yhfK-amplified strain was designated W3110/pSTV-yhfK, and the control pSTV29-introduced strain was designated W3110/pSTV29.

Then, W3110/pSTV-yhfK strain and control W3110/pSTV29 strain were cultured, and the L-glutamic acid-producing ability thereof was examined. W3110/pSTV-yhfK and control W3110/pSTV29 strain were respectively pre-cultured on the L medium (medium containing 10 g of Bacto tryptone, 5 g of yeast extract, 5 g of NaCl and 15 g of agar in 1 L of pure water, pH 7.0) mixed with chloramphenicol, and one loop of cells was inoculated into 5 mL of medium having the following composition by using a 1 µL volume loop provided by Nunc, and cultured at pH 7.0 and 34° C. for 16 hours with shaking.

[Composition of Culture Medium]

| | |
|---|---|
| Glucose | 40 g/L |
| $MgSO_4 \cdot 7H_2O$ | 1.0 g/L |
| $(NH_4)_2SO_4$ | 20 g/L |
| $KH_2PO_4$ | 1.0 g/L |
| Yeast extract | 1.0 g/L |
| $FeSO_4 \cdot 7H_2O$ | 0.01 g/L |
| $MnSO_4 \cdot 5H_2O$ | 0.01 g/L |
| Chloramphenicol | 25 mg/L |
| Calcium carbonate | 30 g/L |
| (adjust to pH 7.0) | |

TABLE 3

Effect of introduction of vector for amplification of yhfK gene derived from Pantoea bacterium into Escherichia bacterium

| 16 hr | OD620 (*1/51) | L-Glutamic acid accumulation (g/L) | Residual sugar (g/L) | Yield (%) |
|---|---|---|---|---|
| W3110 pSTV29 | 0.502 | 1.4 | 5.0 | 3.0 |
| W3110 pSTV-yhfK | 0.448 | 4.6 | 6.5 | 11.8 |

The yield of L-glutamic acid was markedly increased in the Escherichia coli W3110/pSTV-yhfK216 strain having an amplified Pantoea ananatis yhfK gene, as compared with the control W3110/pSTV29 strain.

Example 7

<Production of L-Glutamic Acid by Coryneform Bacterium Strain ATCC13869 or a Derivative of ATCC 13869 which is Amplified with yhfK Gene>

The yhfK gene can be cloned from a chromosomal DNA of the Enterobacteriaceae family such as E. coli or P. ananatis. Based on the nucleotide sequence described in SEQ ID NO: 1 or 3, and using the primers depicted in SEQ ID NO: 5 and NO: 6 or SEQ ID NO: 7 and NO: 8, the yhfK gene can be amplified. The obtained PCR fragment containing yhfK gene is treated with restriction endonuclease, and the treated DNA is inserted into the E. coli-Coryneform shuttle vector pVK9, which is a delivative of pCG1 (U.S. Pat. No. 4,617,267). Thus, plasmid pVK9yhfK is obtained. Transformation of the coryneform L-glutamic acid-producing strain with the pVK9yhfK plasmid can be performed by an ordinary method to obtain the strain containing the amplified yhfK gene. For example, a strain such as the wild-type Corynebacterium glutamicum ATCC13869, the modified strain to increase activities of citrate synthase, phosphoenolpyruvate carboxylase and glutamate dehydrogenase or to decrease α-ketoglutarate dehydrogenase activity could be used as L-glutamate producer of corynebacterium with an amplified yhfK gene.

The yhfK-amplified strain can be grown during for 18-24 hr on CMDX plates (5 g/L of glucose, 10 g/L of peptone, 10 g/L of yeast extract, 1 g/L of $KH_2PO_4$, 0.4 g/L of $MgSO_4 \cdot 7H_2O$, 10 mg/L of $FeSO_4 \cdot 7H_2O$, 10 mg/L of $MnSO_4 \cdot 4$ to $5H_2O$, 3 g/L of urea, 2 g/L (in terms of N amount) of mameno, 20 g/L of agar, pH 7.5), and the cells for ⅙ of each plate can be inoculated into 20 mL of medium (30 g/L of glucose, 15 g/L of $(NH_4)_2SO_4$, 0.4 g/L of $MgSO_4 \cdot 7H_2O$, 1 mg/L of $FeSO_4 \cdot 7H_2O$, 1 mg/L of $MnSO_4 \cdot 4$ to $5H_2O$, 200 µg/L of vitamin B 1, 200 µg/L of biotin, 0.48 g/L (in terms of N amount) of mameno, 1 g/flask of $CaCO_3$, pH 8.0) in a flask and can be cultured at 31.5° C. for 20-40 hours with shaking. Then, concentrations of glucose and L-glutamic acid in the medium can be measured using Biotech Analyzer (Sakura Seiki). Hereby, a strain in which yhfk gene is amplified and has enhanced L-glutamic acid-producing ability is obtained.

INDUSTRIAL APPLICABILITY

By using the microorganism of the present invention, L-glutamic acid can be efficiently produced. L-Glutamic acid is useful as a raw material for seasonings etc.

While the invention has been described in detail with reference to preferred embodiments thereof, it will be apparent to one skilled in the art that various changes can be made, and equivalents employed, without departing from the scope of the invention. Each of the aforementioned documents, including the foreign priority documents, Japanese Patent No. 2004-060542 filed on Mar. 4, 2004, is incorporated by reference herein in its entirety.

The invention claimed is:

1. A microorganism having the ability to produce L-glutamic acid, wherein said microorganism overexpresses the yhfK gene, wherein said yhfK gene encodes a protein selected from the group consisting of:
   (A) a protein comprising the amino acid sequence of SEQ ID NO: 2 or 4; and
   (B) a protein comprising the amino acid sequence of SEQ ID NO: 2 or 4, wherein said protein includes substitution, deletion, insertion or addition of one to 5 amino acids, and wherein said protein has the ability to export L-glutamic acid.

2. A microorganism having the ability to produce L-glutamic acid, wherein said microorganism overexpresses the yhfK, wherein said yhfK gene encodes a protein comprising an amino acid sequence having 95% or more homology to the amino acid sequence of SEQ ID NO: 2 or 4, and wherein said protein has an ability to export L-glutamic acid.

3. A microorganism having the ability to produce L-glutamic acid, wherein said microorganism overexpresses the yhfK gene, which is selected from the group consisting of:
   (a) a DNA comprising the nucleotide sequence from number 1530 to 3620 in SEQ ID NO: 1 or from number 201 to 2288 in SEQ ID NO: 3; and
   (b) a DNA which is able to hybridize to the nucleotide sequence from number 1530 to 3620 in SEQ ID NO: 1 or from number 201 to 2288 in SEQ ID NO: 3, under stringent conditions comprising washing under 0.1× SSC, 0.1% SDS at 68° C., and wherein said DNA encodes a protein which has an ability to export L-glutamic acid.

4. A microorganism having an ability to produce L-glutamic acid, wherein said microorganism overexpresses a yhfK gene, wherein said yhfK gene encodes a protein comprising the amino acid sequence of SEQ ID NO: 10, wherein said protein includes substitution, deletion, insertion, or addition of one to 5 amino acids among the consensus amino acids, and wherein said protein has the ability to export L-glutamic acid.

5. The microorganism according to claim 4, wherein said yhfK gene encodes a protein comprising the amino acid sequence of SEQ ID NO: 10.

6. The microorganism according to claim 5, wherein said microorganism is a γ-proteobacterium.

7. The microorganism according to claim 5, wherein said microorganism is an Enterobacteriaceae selected from the group consisting of *Eseherichia, Enterobacter, Pantoea, Kiebsiella*, and *Serratia*.

8. The microorganism according to claim 5, wherein said microorganism is a *Coryneform* bacterium.

9. A method for producing L-glutamic acid comprising culturing a microorganism according to claim 4 in a medium, and collecting said L-glutamic acid from said medium.

10. The microorganism according to claim 4, wherein said yhfK gene is overexpressed by increasing the copy number of said yhfK gene or by modifying an expression regulatory sequence of said yhfK gene.

11. The microorganism of claim 4, wherein said yhfK gene encodes a protein comprising the amino acid sequence of SEQ ID NO: 2.

12. The microorganism of claim 4, wherein said yhfK gene encodes a protein comprising the amino acid sequence SEQ ID NO: 4.

13. The method of claim 9, wherein said microorganism is cultured under conditions which cause L-glutamic acid to precipitate.

14. The method of claim 13, wherein said conditions comprise a pH of 5.0 to 4.0.

15. A method for producing L-glutamic acid comprising culturing a microorganism according to claim 1 in a medium, and collecting said L-glutamic acid from said medium.

16. A method for producing L-glutamic acid comprising culturing a microorganism according to claim 2 in a medium, and collecting said L-glutamic acid from said medium.

17. A method for producing L-glutamic acid comprising culturing a microorganism according to claim 3 in a medium, and collecting said L-glutamic acid from said medium.

18. A method for producing L-glutamic acid comprising culturing a microorganism according to claim 6 in a medium, and collecting said L-glutamic acid from said medium.

19. A method for producing L-glutamic acid comprising culturing a microorganism according to claim 7 in a medium, and collecting said L-glutamic acid from said medium.

20. A method for producing L-glutamic acid comprising culturing a microorganism according to claim 8 in a medium, and collecting said L-glutamic acid from said medium.

21. A method for producing L-glutamic acid comprising culturing a microorganism according to claim 10 in a medium, and collecting said L-glutamic acid from said medium.

22. A method for producing L-glutamic acid comprising culturing a microorganism according to claim 11 in a medium, and collecting said L-glutamic acid from said medium.

23. A method for producing L-glutamic acid comprising culturing a microorganism according to claim 12 in a medium, and collecting said L-glutamic acid from said medium.

24. A method for producing L-glutamic acid comprising culturing a microorganism according to claim 5 in a medium, and collecting said L-glutamic acid from said medium.

* * * * *

UNITED STATES PATENT AND TRADEMARK OFFICE
CERTIFICATE OF CORRECTION

PATENT NO.         : 7,344,874 B2
APPLICATION NO.    : 11/070085
DATED              : March 18, 2008
INVENTOR(S)        : Hara et al.

Page 1 of 1

It is certified that error appears in the above-identified patent and that said Letters Patent is hereby corrected as shown below:

Title page item 56

Replace the first entry in the Foreign Patent Documents Section as follows:

EP      0 670 370      9/1995

Replace the author of the second entry in the Other Publications Section as follows:

Hoischen, C., et al.,

Signed and Sealed this

Twenty-third Day of September, 2008

JON W. DUDAS
*Director of the United States Patent and Trademark Office*

SEQUENCE LISTING

<160> NUMBER OF SEQ ID NOS: 12

<210> SEQ ID NO 1
<211> LENGTH: 3967
<212> TYPE: DNA
<213> ORGANISM: Pantoea ananatis
<220> FEATURE:
<221> NAME/KEY: CDS
<222> LOCATION: (1530)..(3620)
<223> OTHER INFORMATION:

<400> SEQUENCE: 1

```
gatcgtttat ttccaatatc aacacgctgg ttgtacctgg cgggaaaatg gggctggcga      60
tggaattaat tatggcaccg ctggtaaaac ggctcatgga aggcaaacgc attgaataaa     120
atcagaggcc gcgctggcct ctgaataatt acagctcgat aacttcgtaa ctgtgggtaa     180
tttccacccc tttgcctaac ataatggcaa ccgagcaata cttctcagct gaaaggtcga     240
ccgcacgcgc cacggcttta tctgaaagtg cttttccact gacgataaaa tgcaggttga     300
tgcgggtaaa gatgcgaggc gcttcttccc ggcgttctga ttcgagtttt acttcgcaat     360
cagccacatc gttgcgacct ttttgcaaaa ttgataccac atcaatggcg ctgcatccgc     420
cggccgccat cagcaccatt tccatagggc tgggcgcttt atcgccgaaa ttgccgtcca     480
ttaagacctg atgtccggac gaagactcgc cgaggaatgt taaccettca acccatttga     540
ctcttgcctg cataatctgg ccccagaat gccctgtttt tgcgtcagag tacgcttttg     600
cctggtaaac agcaatccgg agaaatcagc cttattgctg aagcgagaca acacaagaca     660
gtcggcgaaa gctgtgctac aaacagtgct gaaaatattt ttcgtcatcc gaagacgaag     720
ccgggaagaa tgatgcgctc tgcgcaaatg cagcccgaat aatttcctga atggaaacac     780
gcttaacgct ttcatcgcct ggcagggaaa ctgagccctg tattttgggc acgattacaa     840
tagaggataa tagcgaatgg ttctcggcaa accgcaaaca gaccctacac ttgaatggtt     900
cctgtcccat tgccatattc acaagtatcc atccaaaagt acgctgattc accaaggtga     960
aaaagccgaa acgctttact acatcgtgaa aggttccgtc gcggtactga ttaaggatga    1020
agaaggcaaa gagatgattc tttcttatct gaatcaaggc gattttattg gtgagcttgg    1080
cctgtttgaa gaaggtcagg agcgcagcgc ctgggtacgt gcgaaaactg cgtgcgaagt    1140
ggcagagatt tcctacaaga aattccgtca gctcattcag gttaacccgg atattttgat    1200
gcgcctttct tctcagatgg ctcgccgtct gcaggtgacg tcagaaaaag tggggaatct    1260
cgcttttcctg gatgtgaccg gacgcattgc acaaacgttg cttaatctgg ctaaacagcc    1320
agatgccatg acgcatcctg acggcatgca aattaaaatt actcgtcagg aaattggcca    1380
aatcgttggt tgttcacgtg aaaccgtggg ccgtatcttg aagatgctgg aagatcagaa    1440
cctgatctcc gcacacggca aaaccatcgt tgtttacggc acacgctaag cctgactgtt    1500
cacggcgtga tggcgacatt atgccgtga atg tct tgt gtt gag ccg atg tgg      1553
                                 Met Ser Cys Val Glu Pro Met Trp
                                  1               5
cga aga ata atc tat cac ccc gaa gtt aac tat gcg ctg cgc cag acg      1601
Arg Arg Ile Ile Tyr His Pro Glu Val Asn Tyr Ala Leu Arg Gln Thr
         10                  15                  20
ctg gtg ttg tgc ctt ccc gta gcg ctc ggc tgg ctg ttc ggc gat ctg      1649
Leu Val Leu Cys Leu Pro Val Ala Leu Gly Trp Leu Phe Gly Asp Leu
25                  30                  35                  40
caa aaa gga ttg ctg ttc tca ttg gtt ccc gcc tgc tgc aac att gcc      1697
```

```
Gln Lys Gly Leu Leu Phe Ser Leu Val Pro Ala Cys Cys Asn Ile Ala
            45                  50                  55 ggt ctg gac acg ccc cac aaa cgc ttc ttt aaa cgc ctg atc atc ggc     1745
Gly Leu Asp Thr Pro His Lys Arg Phe Phe Lys Arg Leu Ile Ile Gly
         60                  65                  70 ggc agc ctg ttt gcc ctt ggc agt tta ctg atg cag tgg ctg ctg ctt     1793
Gly Ser Leu Phe Ala Leu Gly Ser Leu Leu Met Gln Trp Leu Leu Leu
     75                  80                  85 aaa gac gtg ccg ctg ccg ctc atc ctg ttt gcc ctg cct ttg ctg ctt     1841
Lys Asp Val Pro Leu Pro Leu Ile Leu Phe Ala Leu Pro Leu Leu Leu
 90                  95                 100 ggc gtc acc gga gag atc agt ccg ctg cac gcc cga ctg ctg ccc ggc     1889
Gly Val Thr Gly Glu Ile Ser Pro Leu His Ala Arg Leu Leu Pro Gly
105                 110                 115                 120 acg tta atc gcg gca att ttt acc ctc agc ctg att ggc cgt atg ccc     1937
Thr Leu Ile Ala Ala Ile Phe Thr Leu Ser Leu Ile Gly Arg Met Pro
                125                 130                 135 att tac gtt ccg ccc ctc ctc tat atc ggt gga acg ctc tgg tat ggc     1985
Ile Tyr Val Pro Pro Leu Leu Tyr Ile Gly Gly Thr Leu Trp Tyr Gly
            140                 145                 150 ctg ttc aac tgg ttt tgg ttc tgg ctg tgg aaa gag cag ccg atg cgc     2033
Leu Phe Asn Trp Phe Trp Phe Trp Leu Trp Lys Glu Gln Pro Met Arg
        155                 160                 165 gaa agc ctg agc ctg atc tac cgt gag ctg gca aat tac tgt gac gcc     2081
Glu Ser Leu Ser Leu Ile Tyr Arg Glu Leu Ala Asn Tyr Cys Asp Ala
170                 175                 180 aag tac agc tta ttg acg cag ctg acc gat ccg gaa aaa gcc ctg ccg     2129
Lys Tyr Ser Leu Leu Thr Gln Leu Thr Asp Pro Glu Lys Ala Leu Pro
185                 190                 195                 200 ccc ctg ctg gcg cgt cag caa aaa gcg atc gat ctg atc aac acc tgc     2177
Pro Leu Leu Ala Arg Gln Gln Lys Ala Ile Asp Leu Ile Asn Thr Cys
                205                 210                 215 tat cag caa atg cat atg ctg tct gcg agt cgc gat cac agc cac aaa     2225
Tyr Gln Gln Met His Met Leu Ser Ala Ser Arg Asp His Ser His Lys
            220                 225                 230 cgc ctg acc cgg gcg ttt cag gta gca ctg gat ctg cag gag cat atc     2273
Arg Leu Thr Arg Ala Phe Gln Val Ala Leu Asp Leu Gln Glu His Ile
        235                 240                 245 tcc gtc agc ctg cat cag ccg gaa gag gtc cag aag ctg gtc gag caa     2321
Ser Val Ser Leu His Gln Pro Glu Glu Val Gln Lys Leu Val Glu Gln
250                 255                 260 agc cat gct gaa gcc gtc atc cgc tgg aac gcc aga acg att tca gcc     2369
Ser His Ala Glu Ala Val Ile Arg Trp Asn Ala Arg Thr Ile Ser Ala
265                 270                 275                 280 cgg ctg cgc gcg ctg gcc gac gat att ctg tat cac caa ctc tct ggt     2417
Arg Leu Arg Ala Leu Ala Asp Asp Ile Leu Tyr His Gln Leu Ser Gly
                285                 290                 295 cgt ttc gat atg gac aag cag ttg ggt gcg ctg gag aaa atc gcc ctt     2465
Arg Phe Asp Met Asp Lys Gln Leu Gly Ala Leu Glu Lys Ile Ala Leu
            300                 305                 310 cag cat ccg gac aat ccg gtg ggt aac ttc tgt ctc tat cat ttc agc     2513
Gln His Pro Asp Asn Pro Val Gly Asn Phe Cys Leu Tyr His Phe Ser
        315                 320                 325 cgt atc gcc cgg gtg ctt cga acc caa aag ccg ctt tat caa cgc gac     2561
Arg Ile Ala Arg Val Leu Arg Thr Gln Lys Pro Leu Tyr Gln Arg Asp
330                 335                 340 ctg atg gcc gat cgc cag cgt cgt tta ccg ctg ctg ccc gcg ttg cgg     2609
Leu Met Ala Asp Arg Gln Arg Arg Leu Pro Leu Leu Pro Ala Leu Arg
345                 350                 355                 360
```

```
agc tat ctg tcg ctg cgg tct tcc gca ctg cga acg gcc ggg cgt ttt    2657
Ser Tyr Leu Ser Leu Arg Ser Ser Ala Leu Arg Thr Ala Gly Arg Phe
            365                 370                 375 tcc gtc atg ctg atg ctg ggc agc gcc ctg gcc gtg ttc ttt tcg att    2705
Ser Val Met Leu Met Leu Gly Ser Ala Leu Ala Val Phe Phe Ser Ile
        380                 385                 390 cct aag ccc tac tgg att ttg atg acc atc atg ttt gtc agc cag agc    2753
Pro Lys Pro Tyr Trp Ile Leu Met Thr Ile Met Phe Val Ser Gln Ser
    395                 400                 405 aac tac agc gca acc cgc gta cgt att cag cac cgg gcc ctg gga acc    2801
Asn Tyr Ser Ala Thr Arg Val Arg Ile Gln His Arg Ala Leu Gly Thr
410                 415                 420 ttt gcc gga ctg gct atc gcg gcg gcg tcg cta cgc ctg gat gtg cct    2849
Phe Ala Gly Leu Ala Ile Ala Ala Ala Ser Leu Arg Leu Asp Val Pro
425                 430                 435                 440 gaa ccg ctg gtg ctg agc atc atg ctg gtg att acc ttt atc agc tac    2897
Glu Pro Leu Val Leu Ser Ile Met Leu Val Ile Thr Phe Ile Ser Tyr
                445                 450                 455 cgt ttt acc cgc cag ttt tac ggc tgg tca ata gtg gga ttt acg gtg    2945
Arg Phe Thr Arg Gln Phe Tyr Gly Trp Ser Ile Val Gly Phe Thr Val
            460                 465                 470 acg gcc gtt tat acg ctg caa ctg ctc tcc ctt aac ggg gca cag ttt    2993
Thr Ala Val Tyr Thr Leu Gln Leu Leu Ser Leu Asn Gly Ala Gln Phe
        475                 480                 485 tta ctg ccc cgc ctg ctg gat acg ctg atg ggc tgc ctg atc gcc ttt    3041
Leu Leu Pro Arg Leu Leu Asp Thr Leu Met Gly Cys Leu Ile Ala Phe
    490                 495                 500 ggg ggc atg tta tgg ctg tgg ccg cag tgg caa agt gcc ctg ctg cgc    3089
Gly Gly Met Leu Trp Leu Trp Pro Gln Trp Gln Ser Ala Leu Leu Arg
505                 510                 515                 520 cag aat gcc cat gat gcg ctg gag gcc tgt cag aat gcc ctg cga atg    3137
Gln Asn Ala His Asp Ala Leu Glu Ala Cys Gln Asn Ala Leu Arg Met
                525                 530                 535 ttg ctg ggc cca gag cag tca ccc gat gcg ctg gct tac cag cgg gtt    3185
Leu Leu Gly Pro Glu Gln Ser Pro Asp Ala Leu Ala Tyr Gln Arg Val
            540                 545                 550 aag gtc aac cag gcg cat aac gcc gta ttc aac tcc ctg aat cag gcc    3233
Lys Val Asn Gln Ala His Asn Ala Val Phe Asn Ser Leu Asn Gln Ala
        555                 560                 565 atg cag gag ccg gga ttt aat tca cgc tac ctg cag gat atg cgc tta    3281
Met Gln Glu Pro Gly Phe Asn Ser Arg Tyr Leu Gln Asp Met Arg Leu
    570                 575                 580 tgg gtc acg cac tgc cag ttt atc gtg gag cac att aac gcc atg acc    3329
Trp Val Thr His Cys Gln Phe Ile Val Glu His Ile Asn Ala Met Thr
585                 590                 595                 600 att ctg gca cgt gaa cat acc atg ctg ccg ccc acg ctg gct gag cac    3377
Ile Leu Ala Arg Glu His Thr Met Leu Pro Pro Thr Leu Ala Glu His
                605                 610                 615 tac ctg caa tgg tgc gag atc gcc ctg caa cgg tgt cag caa agg ctg    3425
Tyr Leu Gln Trp Cys Glu Ile Ala Leu Gln Arg Cys Gln Gln Arg Leu
            620                 625                 630 gaa tat gat ggg gaa agt tcg cag acg gat cta cta cag ggc gtg gaa    3473
Glu Tyr Asp Gly Glu Ser Ser Gln Thr Asp Leu Leu Gln Gly Val Glu
        635                 640                 645 gat ata aat gag ggg ccg gtc acg gta ctg gag cag cac gtc agg cgc    3521
Asp Ile Asn Glu Gly Pro Val Thr Val Leu Glu Gln His Val Arg Arg
    650                 655                 660 atc ctg gag cat ctg aaa gtc atg cac acg atc tct tct ctg gcc tgg    3569
Ile Leu Glu His Leu Lys Val Met His Thr Ile Ser Ser Leu Ala Trp
665                 670                 675                 680
```

-continued

```
aac cag cgg cct cat cat ggc cgc tgg ctg ttg cgc agt ctg cgc cgc    3617
Asn Gln Arg Pro His His Gly Arg Trp Leu Leu Arg Ser Leu Arg Arg
            685                 690                 695 aaa taactcaggc agacagcact ttctctaccg cacgggcaaa gcgagccatg         3670
Lys ccctcttcga tatcggcagg ctcgataatc agcgacggtg cgaagcgcat cacatctgtt  3730
ccggccacca gcaccatgac gccttccgca gctgacgcat tcagaatatc gcgcgccttg  3790
cccgcatact gcggcttcag ggctgcacca atcagcaggc ctttaccacg gatatcactg  3850
aacaggtcgt gacgcgcatc aatagccttg agcgcctcaa caaactgctg gcggcggatt  3910
tctaccccat tcagtacagc tggcgtatta ataatatcta acgcggtttc tgcgatc     3967
```

<210> SEQ ID NO 2
<211> LENGTH: 697
<212> TYPE: PRT
<213> ORGANISM: Pantoea ananatis

<400> SEQUENCE: 2

```
Met Ser Cys Val Glu Pro Met Trp Arg Arg Ile Ile Tyr His Pro Glu
1               5                   10                  15

Val Asn Tyr Ala Leu Arg Gln Thr Leu Val Leu Cys Leu Pro Val Ala
            20                  25                  30

Leu Gly Trp Leu Phe Gly Asp Leu Gln Lys Gly Leu Leu Phe Ser Leu
        35                  40                  45

Val Pro Ala Cys Cys Asn Ile Ala Gly Leu Asp Thr Pro His Lys Arg
    50                  55                  60

Phe Phe Lys Arg Leu Ile Ile Gly Gly Ser Leu Phe Ala Leu Gly Ser
65                  70                  75                  80

Leu Leu Met Gln Trp Leu Leu Lys Asp Val Pro Leu Pro Leu Ile
                85                  90                  95

Leu Phe Ala Leu Pro Leu Leu Leu Gly Val Thr Gly Glu Ile Ser Pro
            100                 105                 110

Leu His Ala Arg Leu Leu Pro Gly Thr Leu Ile Ala Ala Ile Phe Thr
        115                 120                 125

Leu Ser Leu Ile Gly Arg Met Pro Ile Tyr Val Pro Pro Leu Leu Tyr
    130                 135                 140

Ile Gly Gly Thr Leu Trp Tyr Gly Leu Phe Asn Trp Phe Trp Phe Trp
145                 150                 155                 160

Leu Trp Lys Glu Gln Pro Met Arg Glu Ser Leu Ser Leu Ile Tyr Arg
                165                 170                 175

Glu Leu Ala Asn Tyr Cys Asp Ala Lys Tyr Ser Leu Leu Thr Gln Leu
            180                 185                 190

Thr Asp Pro Glu Lys Ala Leu Pro Pro Leu Leu Ala Arg Gln Gln Lys
        195                 200                 205

Ala Ile Asp Leu Ile Asn Thr Cys Tyr Gln Gln Met His Met Leu Ser
    210                 215                 220

Ala Ser Arg Asp His Ser His Lys Arg Leu Thr Arg Ala Phe Gln Val
225                 230                 235                 240

Ala Leu Asp Leu Gln Glu His Ile Ser Val Ser Leu His Gln Pro Glu
                245                 250                 255

Glu Val Gln Lys Leu Val Glu Gln Ser His Ala Glu Ala Val Ile Arg
            260                 265                 270

Trp Asn Ala Arg Thr Ile Ser Ala Arg Leu Arg Ala Leu Ala Asp Asp
        275                 280                 285
```

```
Ile Leu Tyr His Gln Leu Ser Gly Arg Phe Asp Met Asp Lys Gln Leu
    290                 295                 300
Gly Ala Leu Glu Lys Ile Ala Leu Gln His Pro Asp Asn Pro Val Gly
305                 310                 315                 320
Asn Phe Cys Leu Tyr His Phe Ser Arg Ile Ala Arg Val Leu Arg Thr
                325                 330                 335
Gln Lys Pro Leu Tyr Gln Arg Asp Leu Met Ala Asp Arg Gln Arg Arg
                340                 345                 350
Leu Pro Leu Leu Pro Ala Leu Arg Ser Tyr Leu Ser Leu Arg Ser Ser
                355                 360                 365
Ala Leu Arg Thr Ala Gly Arg Phe Ser Val Met Leu Met Leu Gly Ser
370                 375                 380
Ala Leu Ala Val Phe Phe Ser Ile Pro Lys Pro Tyr Trp Ile Leu Met
385                 390                 395                 400
Thr Ile Met Phe Val Ser Gln Ser Asn Tyr Ser Ala Thr Arg Val Arg
                405                 410                 415
Ile Gln His Arg Ala Leu Gly Thr Phe Ala Gly Leu Ala Ile Ala Ala
                420                 425                 430
Ala Ser Leu Arg Leu Asp Val Pro Glu Pro Leu Val Leu Ser Ile Met
                435                 440                 445
Leu Val Ile Thr Phe Ile Ser Tyr Arg Phe Thr Arg Gln Phe Tyr Gly
    450                 455                 460
Trp Ser Ile Val Gly Phe Thr Val Thr Ala Val Tyr Thr Leu Gln Leu
465                 470                 475                 480
Leu Ser Leu Asn Gly Ala Gln Phe Leu Leu Pro Arg Leu Leu Asp Thr
                485                 490                 495
Leu Met Gly Cys Leu Ile Ala Phe Gly Gly Met Leu Trp Leu Trp Pro
                500                 505                 510
Gln Trp Gln Ser Ala Leu Leu Arg Gln Asn Ala His Asp Ala Leu Glu
                515                 520                 525
Ala Cys Gln Asn Ala Leu Arg Met Leu Leu Gly Pro Glu Gln Ser Pro
                530                 535                 540
Asp Ala Leu Ala Tyr Gln Arg Val Lys Val Asn Gln Ala His Asn Ala
545                 550                 555                 560
Val Phe Asn Ser Leu Asn Gln Ala Met Gln Glu Pro Gly Phe Asn Ser
                565                 570                 575
Arg Tyr Leu Gln Asp Met Arg Leu Trp Val Thr His Cys Gln Phe Ile
                580                 585                 590
Val Glu His Ile Asn Ala Met Thr Ile Leu Ala Arg Glu His Thr Met
                595                 600                 605
Leu Pro Pro Thr Leu Ala Glu His Tyr Leu Gln Trp Cys Glu Ile Ala
    610                 615                 620
Leu Gln Arg Cys Gln Gln Arg Leu Glu Tyr Asp Gly Glu Ser Ser Gln
625                 630                 635                 640
Thr Asp Leu Leu Gln Gly Val Glu Asp Ile Asn Glu Gly Pro Val Thr
                645                 650                 655
Val Leu Glu Gln His Val Arg Arg Ile Leu Glu His Leu Lys Val Met
                660                 665                 670
His Thr Ile Ser Ser Leu Ala Trp Asn Gln Arg Pro His His Gly Arg
                675                 680                 685
Trp Leu Leu Arg Ser Leu Arg Arg Lys
    690                 695
```

```
<210> SEQ ID NO 3
<211> LENGTH: 2375
<212> TYPE: DNA
<213> ORGANISM: Escherichia coli
<220> FEATURE:
<221> NAME/KEY: CDS
<222> LOCATION: (201)..(2288)
<223> OTHER INFORMATION:

<400> SEQUENCE: 3
gacggtatgc aaatcaaaat tacccgtcag gaaattggtc agattgtcgg ctgttctcgt      60
gaaaccgtgg acgcattct gaagatgctg gaagatcaga acctgatctc cgcacacggt      120
aaaaccatcg tcgtttacgg cactcgttaa tcccgtcgga gtggcgcgtt acctggtagc     180
```
gcgccatttt gtttcccccg atg tgg cgc aga ctg att tat cac ccc gat atc      233
                        Met Trp Arg Arg Leu Ile Tyr His Pro Asp Ile
                         1               5                  10 aac tat gca ctt cga caa acg ctg gtg cta tgt ttg ccc gtg gcc gtt       281
Asn Tyr Ala Leu Arg Gln Thr Leu Val Leu Cys Leu Pro Val Ala Val
            15                  20                  25 ggg tta atg ctt ggc gaa tta cga ttc ggt ctg ctc ttc tcc ctc gtt       329
Gly Leu Met Leu Gly Glu Leu Arg Phe Gly Leu Leu Phe Ser Leu Val
        30                  35                  40 cct gcc tgt tgc aat att gcg ggc ctt gat acg cct cat aaa cgt ttt       377
Pro Ala Cys Cys Asn Ile Ala Gly Leu Asp Thr Pro His Lys Arg Phe
    45                  50                  55 ttc aaa cgc tta atc att ggt gcg tcg ctg ttt gcc acc tgt agc ttg       425
Phe Lys Arg Leu Ile Ile Gly Ala Ser Leu Phe Ala Thr Cys Ser Leu
60                  65                  70                  75 ctg aca cag cta cta ctg gca aaa gat gtt ccc ctg ccc ttt ttg ctg       473
Leu Thr Gln Leu Leu Leu Ala Lys Asp Val Pro Leu Pro Phe Leu Leu
                80                  85                  90 acc gga tta acg ctg gta ctt ggc gtc act gct gag ctg ggg cca ttg       521
Thr Gly Leu Thr Leu Val Leu Gly Val Thr Ala Glu Leu Gly Pro Leu
            95                  100                 105 cac gca aaa ttg ctt cct gca tcg ctg ctc gcc gcc att ttt acc ctc       569
His Ala Lys Leu Leu Pro Ala Ser Leu Leu Ala Ala Ile Phe Thr Leu
        110                 115                 120 agt ttg gcg gga tac atg ccg gtc tgg gaa ccg ttg ctc atc tat gcg       617
Ser Leu Ala Gly Tyr Met Pro Val Trp Glu Pro Leu Leu Ile Tyr Ala
    125                 130                 135 ttg ggc act ctc tgg tac gga ttg ttt aac tgg ttt tgg ttc tgg atc       665
Leu Gly Thr Leu Trp Tyr Gly Leu Phe Asn Trp Phe Trp Phe Trp Ile
140                 145                 150                 155 tgg cgc gaa caa ccg ctg cgc gag tca cta agt ctg ctg tac cgt gaa       713
Trp Arg Glu Gln Pro Leu Arg Glu Ser Leu Ser Leu Leu Tyr Arg Glu
                160                 165                 170 ctg gca gat tat tgt gaa gcc aaa tac agc ctg ctt acc cag cac acc       761
Leu Ala Asp Tyr Cys Glu Ala Lys Tyr Ser Leu Leu Thr Gln His Thr
            175                 180                 185 gac cct gaa aaa gcg ctg ccg ccg ctg ctg gtg cgc cag caa aaa gcg       809
Asp Pro Glu Lys Ala Leu Pro Pro Leu Leu Val Arg Gln Gln Lys Ala
        190                 195                 200 gtc gat cta att acc cag tgc tat cag caa atg cat atg ctt tcc gcg       857
Val Asp Leu Ile Thr Gln Cys Tyr Gln Gln Met His Met Leu Ser Ala
    205                 210                 215 caa aat aat act gac tac aag cgg atg ctg cgt att ttc cag gag gcg       905
Gln Asn Asn Thr Asp Tyr Lys Arg Met Leu Arg Ile Phe Gln Glu Ala
220                 225                 230                 235 ctg gat tta cag gaa cat att tcg gtc agt ttg cat cag ccg gaa gag       953

```
Leu Asp Leu Gln Glu His Ile Ser Val Ser Leu His Gln Pro Glu Glu
                240                 245                 250 gtg caa aag ctg gtc gag cgt agc cat gcg gaa gaa gtt atc cgc tgg        1001
Val Gln Lys Leu Val Glu Arg Ser His Ala Glu Glu Val Ile Arg Trp
            255                 260                 265 aat gcg caa acc gtc gcc gct cgc ctg cgt gtg ctg gct gat gac att        1049
Asn Ala Gln Thr Val Ala Ala Arg Leu Arg Val Leu Ala Asp Asp Ile
        270                 275                 280 ctt tac cat cgc ctg cca acg cgt ttt acg atg gaa aag caa att ggc        1097
Leu Tyr His Arg Leu Pro Thr Arg Phe Thr Met Glu Lys Gln Ile Gly
    285                 290                 295 gca ctg gaa aaa atc gcc cgc cag cat ccg gat aat ccg gtt ggg caa        1145
Ala Leu Glu Lys Ile Ala Arg Gln His Pro Asp Asn Pro Val Gly Gln
300                 305                 310                 315 ttc tgc tac tgg cat ttc agc cgc atc gcc cgc gtg ctg cgc acc caa        1193
Phe Cys Tyr Trp His Phe Ser Arg Ile Ala Arg Val Leu Arg Thr Gln
                320                 325                 330 aaa ccg ctc tat gcc cgt gac tta ctg gcc gat aaa cag cgg cga atg        1241
Lys Pro Leu Tyr Ala Arg Asp Leu Leu Ala Asp Lys Gln Arg Arg Met
            335                 340                 345 cca tta ctt ccg gcg ctg aaa agt tat ctg tca cta aag tct ccg gcg        1289
Pro Leu Leu Pro Ala Leu Lys Ser Tyr Leu Ser Leu Lys Ser Pro Ala
        350                 355                 360 cta cgc aat gcc gga cga ctc agt gtg atg tta agc gtt gcc agc ctg        1337
Leu Arg Asn Ala Gly Arg Leu Ser Val Met Leu Ser Val Ala Ser Leu
    365                 370                 375 atg ggc acc gcg ctg cat ctg ccg aag tcg tac tgg atc ctg atg acg        1385
Met Gly Thr Ala Leu His Leu Pro Lys Ser Tyr Trp Ile Leu Met Thr
380                 385                 390                 395 gta ttg ctg gtg aca caa aat ggc tat ggc gca acc cgt ctg agg att        1433
Val Leu Leu Val Thr Gln Asn Gly Tyr Gly Ala Thr Arg Leu Arg Ile
                400                 405                 410 gtg aat cgc tcc gtg gga acc gtg gtc ggg tta atc att gcg ggc gtg        1481
Val Asn Arg Ser Val Gly Thr Val Val Gly Leu Ile Ile Ala Gly Val
            415                 420                 425 gcg ctg cac ttt aaa att ccc gaa ggt tac acc ctg acg ttg atg ctg        1529
Ala Leu His Phe Lys Ile Pro Glu Gly Tyr Thr Leu Thr Leu Met Leu
        430                 435                 440 att acc acc ctc gcc agc tac ctg ata ttg cgc aaa aac tac ggc tgg        1577
Ile Thr Thr Leu Ala Ser Tyr Leu Ile Leu Arg Lys Asn Tyr Gly Trp
    445                 450                 455 gcg acg gtc ggt ttt act att acc gca gtg tat acc ctg caa cta ttg        1625
Ala Thr Val Gly Phe Thr Ile Thr Ala Val Tyr Thr Leu Gln Leu Leu
460                 465                 470                 475 tgg ttg aac ggc gag caa tac atc ctt ccg cgt ctt atc gat acc att        1673
Trp Leu Asn Gly Glu Gln Tyr Ile Leu Pro Arg Leu Ile Asp Thr Ile
                480                 485                 490 att ggt tgt tta att gct ttc ggc ggt act gtc tgg ctg tgg ccg cag        1721
Ile Gly Cys Leu Ile Ala Phe Gly Gly Thr Val Trp Leu Trp Pro Gln
            495                 500                 505 tgg cag agc ggg tta ttg cgt aaa aac gcc cat gat gct tta gaa gcc        1769
Trp Gln Ser Gly Leu Leu Arg Lys Asn Ala His Asp Ala Leu Glu Ala
        510                 515                 520 tat cag gaa gcg att cgc ttg att ctt agc gag gat ccg caa cct acg        1817
Tyr Gln Glu Ala Ile Arg Leu Ile Leu Ser Glu Asp Pro Gln Pro Thr
    525                 530                 535 cca ctg gcc tgg cag cga atg cgg gta aat cag gca cat aac act ctg        1865
Pro Leu Ala Trp Gln Arg Met Arg Val Asn Gln Ala His Asn Thr Leu
540                 545                 550                 555
```

-continued

| | | | | | | | | | | | | | | | | |
|---|---|---|---|---|---|---|---|---|---|---|---|---|---|---|---|---|
| tat | aac | tca | ttg | aat | cag | gcg | atg | cag | gaa | ccg | gcg | ttt | aac | agc | cat | 1913 |
| Tyr | Asn | Ser | Leu | Asn | Gln | Ala | Met | Gln | Glu | Pro | Ala | Phe | Asn | Ser | His | |
| | | | | 560 | | | | | 565 | | | | | 570 | | |
| tat | ctg | gca | gat | atg | aaa | ctg | tgg | gta | acg | cac | agc | cag | ttt | att | gtt | 1961 |
| Tyr | Leu | Ala | Asp | Met | Lys | Leu | Trp | Val | Thr | His | Ser | Gln | Phe | Ile | Val | |
| | | | 575 | | | | | 580 | | | | | 585 | | | |
| gag | cat | att | aat | gcc | atg | acc | acg | ctg | gcg | cgg | gaa | cac | cgg | gca | ttg | 2009 |
| Glu | His | Ile | Asn | Ala | Met | Thr | Thr | Leu | Ala | Arg | Glu | His | Arg | Ala | Leu | |
| | | | 590 | | | | | 595 | | | | | 600 | | | |
| cca | cct | gaa | ctg | gca | caa | gag | tat | tta | cag | tct | tgt | gaa | atc | gcc | att | 2057 |
| Pro | Pro | Glu | Leu | Ala | Gln | Glu | Tyr | Leu | Gln | Ser | Cys | Glu | Ile | Ala | Ile | |
| | | 605 | | | | | 610 | | | | | 615 | | | | |
| cag | cgt | tgt | cag | cag | cga | ctg | gag | tat | gac | gaa | ccg | ggt | agt | tct | ggc | 2105 |
| Gln | Arg | Cys | Gln | Gln | Arg | Leu | Glu | Tyr | Asp | Glu | Pro | Gly | Ser | Ser | Gly | |
| 620 | | | | | 625 | | | | | 630 | | | | | 635 | |
| gat | gcc | aat | atc | atg | gat | gcg | ccg | gag | atg | cag | ccg | cac | gaa | ggc | gcg | 2153 |
| Asp | Ala | Asn | Ile | Met | Asp | Ala | Pro | Glu | Met | Gln | Pro | His | Glu | Gly | Ala | |
| | | | | 640 | | | | | 645 | | | | | 650 | | |
| gca | ggt | acg | ctg | gag | cag | cat | tta | cag | cgg | gtt | att | ggt | cat | ctg | aac | 2201 |
| Ala | Gly | Thr | Leu | Glu | Gln | His | Leu | Gln | Arg | Val | Ile | Gly | His | Leu | Asn | |
| | | | | 655 | | | | | 660 | | | | | 665 | | |
| acc | atg | cac | acc | att | tcg | tcg | atg | gca | tgg | cgt | cag | cga | ccg | cat | cac | 2249 |
| Thr | Met | His | Thr | Ile | Ser | Ser | Met | Ala | Trp | Arg | Gln | Arg | Pro | His | His | |
| | | | 670 | | | | | 675 | | | | | 680 | | | |
| ggg | att | tgg | ctg | agt | cgc | aag | ttg | cgg | gat | tcg | aag | gcg | taatgcaggc | | | 2298 |
| Gly | Ile | Trp | Leu | Ser | Arg | Lys | Leu | Arg | Asp | Ser | Lys | Ala | | | | |
| | | 685 | | | | | 690 | | | | | 695 | | | | | taaaccatcg gataaggcat tcacgccgca tccgacatct tttgcctgat gcttcgtatt 2358 tacgccccaa ccaccttt 2375

<210> SEQ ID NO 4
<211> LENGTH: 696
<212> TYPE: PRT
<213> ORGANISM: Escherichia coli

<400> SEQUENCE: 4

Met Trp Arg Arg Leu Ile Tyr His Pro Asp Ile Asn Tyr Ala Leu Arg
1               5                   10                  15

Gln Thr Leu Val Leu Cys Leu Pro Val Ala Val Gly Leu Met Leu Gly
            20                  25                  30

Glu Leu Arg Phe Gly Leu Leu Phe Ser Leu Val Pro Ala Cys Cys Asn
        35                  40                  45

Ile Ala Gly Leu Asp Thr Pro His Lys Arg Phe Phe Lys Arg Leu Ile
    50                  55                  60

Ile Gly Ala Ser Leu Phe Ala Thr Cys Ser Leu Leu Thr Gln Leu Leu
65                  70                  75                  80

Leu Ala Lys Asp Val Pro Leu Pro Phe Leu Leu Thr Gly Leu Thr Leu
                85                  90                  95

Val Leu Gly Val Thr Ala Glu Leu Gly Pro Leu His Ala Lys Leu Leu
            100                 105                 110

Pro Ala Ser Leu Leu Ala Ala Ile Phe Thr Leu Ser Leu Ala Gly Tyr
        115                 120                 125

Met Pro Val Trp Glu Pro Leu Leu Ile Tyr Ala Leu Gly Thr Leu Trp
    130                 135                 140

Tyr Gly Leu Phe Asn Trp Phe Trp Phe Trp Ile Trp Arg Glu Gln Pro
145                 150                 155                 160

Leu Arg Glu Ser Leu Ser Leu Leu Tyr Arg Glu Leu Ala Asp Tyr Cys

-continued

```
            165                 170                 175
Glu Ala Lys Tyr Ser Leu Leu Thr Gln His Thr Asp Pro Glu Lys Ala
        180                 185                 190
Leu Pro Pro Leu Leu Val Arg Gln Gln Lys Ala Val Asp Leu Ile Thr
        195                 200                 205
Gln Cys Tyr Gln Gln Met His Met Leu Ser Ala Gln Asn Asn Thr Asp
        210                 215                 220
Tyr Lys Arg Met Leu Arg Ile Phe Gln Glu Ala Leu Asp Leu Gln Glu
225                 230                 235                 240
His Ile Ser Val Ser Leu His Gln Pro Glu Glu Val Gln Lys Leu Val
                245                 250                 255
Glu Arg Ser His Ala Glu Glu Val Ile Arg Trp Asn Ala Gln Thr Val
            260                 265                 270
Ala Ala Arg Leu Arg Val Leu Ala Asp Asp Ile Leu Tyr His Arg Leu
        275                 280                 285
Pro Thr Arg Phe Thr Met Glu Lys Gln Ile Gly Ala Leu Glu Lys Ile
        290                 295                 300
Ala Arg Gln His Pro Asp Asn Pro Val Gly Gln Phe Cys Tyr Trp His
305                 310                 315                 320
Phe Ser Arg Ile Ala Arg Val Leu Arg Thr Gln Lys Pro Leu Tyr Ala
                325                 330                 335
Arg Asp Leu Leu Ala Asp Lys Gln Arg Arg Met Pro Leu Leu Pro Ala
            340                 345                 350
Leu Lys Ser Tyr Leu Ser Leu Lys Ser Pro Ala Leu Arg Asn Ala Gly
        355                 360                 365
Arg Leu Ser Val Met Leu Ser Val Ala Ser Leu Met Gly Thr Ala Leu
        370                 375                 380
His Leu Pro Lys Ser Tyr Trp Ile Leu Met Thr Val Leu Leu Val Thr
385                 390                 395                 400
Gln Asn Gly Tyr Gly Ala Thr Arg Leu Arg Ile Val Asn Arg Ser Val
                405                 410                 415
Gly Thr Val Val Gly Leu Ile Ile Ala Gly Val Ala Leu His Phe Lys
            420                 425                 430
Ile Pro Glu Gly Tyr Thr Leu Thr Leu Met Leu Ile Thr Thr Leu Ala
        435                 440                 445
Ser Tyr Leu Ile Leu Arg Lys Asn Tyr Gly Trp Ala Thr Val Gly Phe
        450                 455                 460
Thr Ile Thr Ala Val Tyr Thr Leu Gln Leu Leu Trp Leu Asn Gly Glu
465                 470                 475                 480
Gln Tyr Ile Leu Pro Arg Leu Ile Asp Thr Ile Ile Gly Cys Leu Ile
                485                 490                 495
Ala Phe Gly Gly Thr Val Trp Leu Trp Pro Gln Trp Gln Ser Gly Leu
            500                 505                 510
Leu Arg Lys Asn Ala His Asp Ala Leu Glu Ala Tyr Gln Glu Ala Ile
        515                 520                 525
Arg Leu Ile Leu Ser Glu Asp Pro Gln Pro Thr Pro Leu Ala Trp Gln
        530                 535                 540
Arg Met Arg Val Asn Gln Ala His Asn Thr Leu Tyr Asn Ser Leu Asn
545                 550                 555                 560
Gln Ala Met Gln Glu Pro Ala Phe Asn Ser His Tyr Leu Ala Asp Met
                565                 570                 575
Lys Leu Trp Val Thr His Ser Gln Phe Ile Val Glu His Ile Asn Ala
            580                 585                 590
```

-continued

```
Met Thr Thr Leu Ala Arg Glu His Arg Ala Leu Pro Pro Glu Leu Ala
            595                 600                 605
Gln Glu Tyr Leu Gln Ser Cys Glu Ile Ala Ile Gln Arg Cys Gln Gln
        610                 615                 620
Arg Leu Glu Tyr Asp Glu Pro Gly Ser Ser Gly Asp Ala Asn Ile Met
625                 630                 635                 640
Asp Ala Pro Glu Met Gln Pro His Glu Gly Ala Ala Gly Thr Leu Glu
                645                 650                 655
Gln His Leu Gln Arg Val Ile Gly His Leu Asn Thr Met His Thr Ile
            660                 665                 670
Ser Ser Met Ala Trp Arg Gln Arg Pro His His Gly Ile Trp Leu Ser
        675                 680                 685
Arg Lys Leu Arg Asp Ser Lys Ala
    690                 695

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
tcaaggcgat tttattgggt gagcttggc                                 29

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
ttattaatac gccagctgta ctgaatgggg                                30

<210> SEQ ID NO 7
<211> LENGTH: 40
<212> TYPE: DNA
<213> ORGANISM: Artificial Sequence
<220> FEATURE:
<223> OTHER INFORMATION: Primer

<400> SEQUENCE: 7
gatcctgcag gtcaggaaat cggtcagatt gtcggctgtt                     40

<210> SEQ ID NO 8
<211> LENGTH: 40
<212> TYPE: DNA
<213> ORGANISM: Artificial Sequence
<220> FEATURE:
<223> OTHER INFORMATION: Primer

<400> SEQUENCE: 8
gatcgaattc aaggtggttg gggcgtaaat acgaagcatc                     40

<210> SEQ ID NO 9
<211> LENGTH: 16214
<212> TYPE: DNA
<213> ORGANISM: Artificial Sequence
<220> FEATURE:
<223> OTHER INFORMATION: Plasmid

<400> SEQUENCE: 9
```

```
gaattccgcc agaaccttca tcagcagcat aaacaggtgc agtgaacagc agagatacgg      60
ccagtgcggc caatgttttt tgtcctttaa acataacaga gtcctttaag gatatagaat     120
aggggtatag ctacgccaga atatcgtatt tgattattgc tagttttag ttttgcttaa      180 aaaatattgt tagttttatt aaattggaaa actaaattat tggtatcatg aattgttgta     240
tgatgataaa tataggggg atatgataga cgtcattttc atagggttat aaaatgcgac      300
taccatgaag ttttaattc aaagtattgg gttgctgata atttgagctg ttctattctt      360
tttaaatatc tatataggtc tgttaatgga ttttattttt acaagttttt tgtgtttagg     420
catataaaaa tcaagcccgc catatgaacg gcgggttaaa atatttacaa cttagcaatc     480
gaaccattaa cgcttgatat cgcttttaaa gtcgcgtttt tcatatcctg tatacagctg     540
acgcggacgg gcaatcttca taccgtcact gtgcatttcg ctccagtggg cgatccagcc     600
aacggtacgt gccattgcga aaatgacggg gaacatggaa gacggaatac ccatcgcttt     660
caggatgata ccagagtaga aatcgacgtt cgggtacagt ttcttctcga taaagtacgg     720
gtcgttcagc gcgatgtttt ccagctccat agccacttcc agcaggtcat ccttcgtgcc     780
cagctctttc agcacttcat ggcaggtttc acgcattacg gtggcgcgcg ggtcgtaatt     840
tttgtacacg cggtgaccga agcccatcag gcggaaagaa tcattttgt ctttcgcacg      900 acgaaaaaat tccggaatgt gtttaacgga gctgatttct tccagcattt tcagcgccgc     960
ttcgttagca ccgccgtgcg caggtcccca cagtgaagca atacctgctg cgatacaggc    1020
aaacgggttc gcacccgaag agccagcggt acgcacggtg gaggtagagg cgttctgttc    1080
atggtcagcg tgcaggatca gaataccggtc catagcacgt tccagaatcg gattaacttc    1140
atacggttcg cacggcgtgg agaacatcat attcaggaag ttaccggcgt aggagagatc    1200
gttgcgcggg taaacaaatg gctgaccaat ggaatacttg taacacatcg cggccatggt    1260
cggcattttc gacagcaggc ggaacgcggc aatttcacgg tgacgaggat tgttaacatc    1320
cagcgagtcg tgatagaacg ccgccagcgc gccggtaata ccacacatga ctgccattgg    1380
atgcgagtcg cgacggaaag catggaacag acgggtaatc tgctcgtgga tcatggtatg    1440
acgggtcacc gtagttttaa attcgtcata ctgttcctga gtcggttttt caccattcag    1500
caggatgtaa caaacttcca ggtagttaga atcggtcgcc agctgatcga tcgggaaacc    1560
gcggtgcagc aaaataccttt catcaccatc aataaaagta attttagatt cgcaggatgc    1620
ggttgaagtg aagcctgggt caaaggtgaa cacaccttttt gaaccgagag tacgatatc    1680 aataacatct tgacccagcg tgcctttcag cacatccagt tcaacagctg tatccccgtt    1740
gagggtgagt tttgcttttg tatcagccat ttaaggtctc cttagcgcct tattgcgtaa    1800
gactgccgga acttaaattt gccttcgcac atcaacctgg ctttacccgt ttttattttg    1860
gctcgccgct ctgtgaaaga ggggaaaacc tgggtacaga gctctgggcg cttgcaggta    1920
aaggatccat tgatgacgaa taaatggcga atcaagtact tagcaatccg aattattaaa    1980
cttgtctacc actaataact gtcccgaatg aattggtcaa tactccacac tgttacataa    2040
gttaatctta ggtgaaatac cgacttcata acttttacgc attatatgct tttcctggta    2100
atgtttgtaa caactttgtt gaatgattgt caaattagat gattaaaaat taaataaatg    2160
ttgttatcgt gacctggatc actgttcagg ataaacccg acaaactata tgtaggttaa     2220
ttgtaatgat tttgtgaaca gcctatactg ccgccagtct ccggaacacc ctgcaatccc    2280
gagccaccca gcgttgtaac gtgtcgtttt cgcatctgga agcagtgttt tgcatgacgc    2340
```

```
gcagttatag aaaggacgct gtctgacccg caagcagacc ggaggaagga aatcccgacg   2400
tcggggatcc tctagagctt tagcgtctga ggttatcgca atttggttat gagattactc   2460
tcgttattaa tttgctttcc tgggtcattt ttttcttgct taccgtcaca ttcttgatgg   2520
tatagtcgaa aactgcaaaa gcacatgaca taaacaacat aagcacaatc gtattaatat   2580
ataagggttt tatatctatg gatcagacat attctctgga gtcattcctc aaccatgtcc   2640
aaaagcgcga cccgaatcaa accgagttcg cgcaagccgt tcgtgaagta atgaccacac   2700
tctggccttt tcttgaacaa atccaaaat atcgccagat gtcattactg gagcgtctgg   2760
ttgaaccgga gcgcgtgatc cagtttcgcg tggtatgggt tgatgatcgc aaccagatac   2820
aggtcaaccg tgcatggcgt gtgcagttca gctctgccat cggcccgtac aaaggcggta   2880
tgcgcttcca tccgtcagtt aacctttcca ttctcaaatt cctcggcttt gaacaaacct   2940
tcaaaaatgc cctgactact ctgccgatgg gcggtggtaa aggcggcagc gatttcgatc   3000
cgaaaggaaa aagcgaaggt gaagtgatgc gtttttgcca ggcgctgatg actgaactgt   3060
atcgccacct gggcgcggat accgacgttc cggcaggtga tatcggggtt ggtggtcgtg   3120
aagtcggctt tatggcgggg atgatgaaaa agctctccaa caataccgcc tgcgtcttca   3180
ccggtaaggg ccttttcattt ggcggcagtc ttattcgccc ggaagctacc ggctacggtc   3240
tggtttattt cacagaagca atgctaaaac gccacggtat gggttttgaa gggatgcgcg   3300
tttccgtttc tggctccggc aacgtcgccc agtacgctat cgaaaagcg atggaatttg   3360 gtgctcgtgt gatcactgcg tcagactcca gcggcactgt agttgatgaa gcggattca   3420 cgaaagagaa actggcacgt cttatcgaaa tcaaagccag ccgcgatggt cgagtggcag   3480
attacgccaa agaatttggt ctggtctatc tcgaaggcca acagccgtgg tctctaccgg   3540
ttgatatcgc cctgccttgc gccacccaga atgaactgga tgttgacgcc gcgcatcagc   3600
ttatcgctaa tggcgttaaa gccgtcgccg aaggggcaaa tatgccgacc accatcgaag   3660
cgactgaact gttccagcag gcaggcgtac tatttgcacc gggtaaagcg gctaatgctg   3720
gtggcgtcgc tacatcgggc ctggaaatgc acaaaacgc tgcgcgcctg ggctggaaag   3780
ccgagaaagt tgacgcacgt ttgcatcaca tcatgctgga tatccaccat gcctgtgttg   3840
agcatggtgg tgaaggtgag caaaccaact acgtgcaggg cgcgaacatt gccggttttg   3900
tgaaggttgc cgatgcgatg ctggcgcagg gtgtgattta agttgtaaat gcctgatggc   3960
gctacgctta tcaggcctac aaatgggcac aattcattgc agttacgctc taatgtaggc   4020
cgggcaagcg cagcgccccc ggcaaaattt caggcgttta tgagtattta acggatgatg   4080
ctccccacgg aacatttctt atgggccaac ggcatttctt actgtagtgc tcccaaaact   4140
gcttgtcgta acgataacac gcttcaagtt cagcatccgt taactttctg cggactcacg   4200
cgcgcagcac tatgccagta aagaaatccc atttgactat tttttgata atcttcttcg   4260 cttttcgaaca actcgtgcgc ctttcgagaa gctagagtcg actcgccaat caccagcact   4320
aaagtgcgcg gttcgttacc cgattcatct ttgaaattag ccagtggcgg caaggcatta   4380
ttttcattca gtaactttgt tagcgagttt agttgctgac gatactgata atagccggtc   4440
aggaattgcc acgtgcggc aggctccata cgcgaggcca ggttatccaa cgttttctca   4500
aacggcttgt ttttgataaa cgtattcatg gcgatcggat gcagaatcaa gccataaagc   4560
agggcaaaag agacaacata acgccacggc tttggaatat agaccgggcg caggcgtgtc   4620
cacagcagaa ctgccaccgc cgtataggcc agcgcgataa gcacaatttt caggctgaaa   4680
tactggctta aatactcgct ggcttcgttg gtgttggttt cgaacatcac aaacagaacg   4740
```

```
ctctgcgaga actcctgacc gtagatgacg tagtagcaca gcgccgccag agaggccgcc    4800
catagcacca cgccgattac tgcggcaata attttaatcc gcttcggaaa gaggaatacc    4860
gggatcaacc acagcgaact gaataacagc gagtcgcgaa tgccgttagt gccactataa    4920
ccactgatgt aaataatggc ctgtagcaga gtagagaaaa accaaaagta gagcagtgcc    4980
caacccaggg ctttccagct aaaaagaggt ttagcctgga cttctgtgga atgcatagta    5040
agaacctgtc ttgaaaaaat atcgccgaat gtaacgacaa ttccttaagg atatctgaag    5100
gtatattcag aatttgaata aaatgcagac agaaatatat tgaaaacgag ggtgttagaa    5160
cagaagtatt tcagaaaacc ctcgcgcaaa agcacgaggg tttgcagaag aggaagatta    5220
gccggtatta cgcatacctg ccgcaatccc ggcaatagtg accattaacg cttgttcgac    5280
gcgaggatcc ggttcctggc cttctttttc tgcctggcgg gagcggtgca gcaactcggc    5340
ctgcaatacg ttcagcgggt cggtgtaaat attccgtagc tgaatagact ctgcaatcca    5400
cggcagatcg gccatcagat gggaatcgtt ggcaatcgcc agcaccactt tgatgtcttc    5460
ttcttgcagg ttgcgtaact ctttacctaa cggccacagt gctttgtcta ccaggcgttg    5520
gtcatagtat tccgccagcc acaggtctgc tttggcgaag accatctcca gcatgccgag    5580
acgcgtcgag aagaatggcc aatcgcggca catagcctcc agctcgctct gtttgccgtc    5640
ttcgaccact ttttgcagcg ccgtacctgc acccagccag gcggggagca tcagacggtt    5700
ttgcgtccag gcgaagatcc acggaatggc gcgtagtgac tcgacgccgc cggttgggcg    5760
acgtttcgcc ggacgtgaac ccaacggcag tttgcccagt tcttgttccg gcgtagcgga    5820
gcggaagtaa ggcacaaaat cttttgttttc acgtacgtag ccgcggtaga catcgcagga    5880
gatgactgac agttcatcca taatgcgacg ccagctctct ttcggctccg gcggtggcag    5940
caggttggct tccagaatcg ccccggtata aagcgacagg ctgctgacgg tgatttctgg    6000
cagaccatat ttaaagcgga tcatctcgcc ctgttcggtt acgcgcaggc cgcctttcag    6060
gcttcctggc ggttgtgaca gcagcgccgc atgagcaggt gcgccgccgc gaccaatgga    6120
accgccgcga ccgtggaaca acgtcagctc aatacccgct ttttcgcagg ttttgattaa    6180
tgcatcctgt gcctgatatt gcgcccagga agctgccatc actcccgcat cttttgctga    6240
gtcggaatag ccaatcatca ccatctgttt gccctgaatc aggccacgat accagtcaat    6300
attgagcagc tgggtcatga catcgttggc gttgttcaga tcatcgaggg tttcaaacag    6360
cggagcaacc ggcatcgcaa acccgatacc cgcttctttc agcagcaggt ggacagccag    6420
tacgtcggac ggcgttttcg ccatcgagat cacgtaggcg gcaatggagc cttgcggtgc    6480
ttcggcaatc acctgcagg tatcgagcac ttcgcgcgtt tcggcgcttg gttgccagtt    6540
gcgcggcaga agcggacgtt tggagttcag ttcgcggatc aggaacgcct gtttgtcggc    6600
ctctgaccag ctttcgtagt cgccgatacc gaggtagcgg gtcagctcgc ccagcgcttc    6660
ggtatgacgc gtgctctcct gacggatatc aatacggacc agcggtacgc cgaaacattt    6720
cacgcggcgc agggtgtcga gcagatcgcc gttggcgata taccatgc cacacgcctg    6780
aagtgactgg tagcaagcgt agagcggttc ccacagttct tcgttttgtg tcagcaggcc    6840
ttctggtttt ggcagttctt cgcctttcag gcgcgcttcc agccatgcct gtgtcgccat    6900
caggcgagaa cgcaggtttt tcatcagata gcgatacggt tctgcggcac cttcttcgcc    6960
aaccagcgcc agcagttcag gggtcgcttc aaccatcgac agttcagaaa ccagcacctg    7020
aatatctttc aggaacaaat cggtggcttt ccagcggctg agtagcagga cgtggcgggt    7080
```

```
gatatcggca gtgacgttcg ggttgccgtc gcggtcgccg cccatccacg aagtaaaacg    7140
gaccggaaca aattcgacgg gcagtttgta gccgaggttc tcttccagtt gttcgttcag    7200
ttcgcgcagg taatttggta cgccttgcca caggctgttt tccactacgg caaagcccca    7260
tttggcttca tctaccgggc ttggacgcag cttacggatt tcatcggtat gccatgactg    7320
ggcgatcaac tggcgcaggc gacgcatcag ctggttgtgt tcgtagtcag cgatatcttt    7380
gttatcgagc tgttttaaac aggcgttcac ttccaccatt ttgtggatca gtgtacgacg    7440
ggtaatttcg gttgggtgag ccgtgaggac cagttccagc gacagcgatt ccactgcttt    7500
tttgatggtg tcttcgctca gttccggctg gtttttcagt ttacgcaggg tgcgggcgat    7560
cacttccggg ttgctggcag cttcgccttt cggcgaaatg ctgtggtatt gctcggcggt    7620
gttggccagg ttcaggaact gactaaacgc acgcgcaacg ggcagcagct cgtcgttcga    7680
caaattttgt aaggtggtga gcaactcctg gcggttagca tcattgccag cgcgtgaaga    7740
tttcgacaac ttacggatag tttctacgcg ttcaagaatg tgttctccca acgcatcctt    7800
gatggtttct cccagcactt tgccgagcat actgacatta ctacgcaatg cggaatattg    7860
ttcgttcata ttaccccaga caccccatct tatcgtttga tagccctgta tccttcacgt    7920
cgcattggcg cgaatatgct cgggctttgc ttttcgtcgt cttttataaa gccacgtaaa    7980
agcggtgacg tcaaatgctg cgaaatcgct tcagcaaacg aataaatagc aggaatttac    8040
gtcattaaat tcacgacgct ttaaataagc gtaacttatg gaaatgttaa aaaatcgccc    8100
caagtaacac caaaggtgta ggtcggataa gatgcgcaag tatcgcatcc gacattattg    8160
cggcactgga gtttggcaac agtgccggat gcggcgcgag cgccttatcc ggcctacagt    8220
tgggcatcgt ttgagtcact gtcggtcgga taagatgcgc aagtatcgca tccgacatta    8280
ttgcggcact ggagtttggc aacagtgccg gatgcggcgc gagcgcctta tccggcctac    8340
ggttgggcat cgtttgagtc actgtaggtc ggataagatg cgcaagcatc gcatccgaca    8400
ttattgcggc actggagttt ggcaacagcg ccggatgcgg cgcgagcgcc ttatccggcc    8460
tacgttttaa tgccagcaaa aatggtgaat tacctgggtt atcagttcgc gggtgggctt    8520
gataaaccgt gtttccagat attcatcagg ttgatgagcc tgattaattg agccaggccc    8580
caacaccagc gtcgggcata acgtttgaat aaacggcgct tcggtacagt agttcaccac    8640
ttcggttttt gctccgagca atttctcaac cacttcaacc agttgatgat tcggtgggca    8700
ttcatagcca gggatcggcg gatgcagctc gtcgacctgc aggagcagaa gagcatacat    8760
ctggaagcaa agccaggaaa gcggcctatg gagctgtgcg gcagcgctca gtaggcaatt    8820
tttcaaaata ttgttaagcc ttttctgagc atggtatttt tcatggtatt accaattagc    8880
aggaaaataa gccattgaat ataaaagata aaaatgtctt gttacaata gagtgggggg    8940
ggtcagcctg ccgccttggg ccgggtgatg tcgtacttgc ccgccgcgaa ctcggttacc    9000
gtccagccca gcgcgaccag ctccggcaac gcctcgcgca cccgctggcg gcgcttgcgc    9060
atggtcgaac cactggcctc tgacggccag acatagccgc acaaggtatc tatggaagcc    9120
ttgccggttt tgccggggtc gatccagcca cacagccgct ggtgcagcag gcgggcggtt    9180
tcgctgtcca gcgcccgcac ctcgtccatg ctgatgcgca catgctggcc gccacccatg    9240
acggcctgcg cgatcaaggg gttcagggcc acgtacaggc gcccgtccgc ctcgtcgctg    9300
gcgtactccg acagcagccg aaaccccctgc cgcttgcggc cattctgggc gatgatggat    9360
accttccaaa ggcgctcgat gcagtcctgt atgtgcttga gcgccccacc actatcgacc    9420
tctgccccga tttcctttgc cagcgcccga tagctacctt tgaccacatg gcattcagcg    9480
```

-continued

| | | | | | |
|---|---|---|---|---|---|
| gtgacggcct | cccacttggg | ttccaggaac | agccggagct | gccgtccgcc | ttcggtcttg | 9540 |
| ggttccgggc | caagcactag | gccattaggc | ccagccatgg | ccaccagccc | ttgcaggatg | 9600 |
| cgcagatcat | cagcgcccag | cggctccggg | ccgctgaact | cgatccgctt | gccgtcgccg | 9660 |
| tagtcatacg | tcacgtccag | cttgctgcgc | ttgcgctcgc | cccgcttgag | ggcacggaac | 9720 |
| aggccggggg | ccagacagtg | cgccgggtcg | tgccggacgt | ggctgaggct | gtgcttgttc | 9780 |
| ttaggcttca | ccacggggca | ccccttgct | cttgcgctgc | ctctccagca | cggcgggctt | 9840 |
| gagcaccccg | ccgtcatgcc | gcctgaacca | ccgatcagcg | aacggtgcgc | catagttggc | 9900 |
| cttgctcaca | ccgaagcgga | cgaagaaccg | gcgctggtcg | tcgtccacac | cccattcctc | 9960 |
| ggcctcggcg | ctggtcatgc | tcgacaggta | ggactgccag | cggatgttat | cgaccagtac | 10020 |
| cgagctgccc | cggctggcct | gctgctggtc | gcctgcgccc | atcatggccg | cgcccttgct | 10080 |
| ggcatggtgc | aggaacacga | tagagcaccc | ggtatcggcg | gcgatggcct | ccatgcgacc | 10140 |
| gatgacctgg | gccatggggc | cgctggcgtt | ttcttcctcg | atgtggaacc | ggcgcagcgt | 10200 |
| gtccagcacc | atcaggcggc | ggccctcggc | ggcgcgcttg | aggccgtcga | accactccgg | 10260 |
| ggccatgatg | ttgggcaggc | tgccgatcag | cggctggatc | agcaggccgt | cagccacggc | 10320 |
| ttgccgttcc | tcggcgctga | ggtgcgcccc | aagggcgtgc | aggcggtgat | gaatggcggt | 10380 |
| gggcgggtct | tcggcgggca | ggtagatcac | cgggccggtg | ggcagttcgc | ccacctccag | 10440 |
| cagatccggc | ccgcctgcaa | tctgtgcggc | cagttgcagg | gccagcatgg | atttaccggc | 10500 |
| accaccgggc | gacaccagcg | ccccgaccgt | accggccacc | atgttgggca | aaacgtagtc | 10560 |
| cagcggtggc | ggcgctgctg | cgaacgcctc | cagaatattg | ataggcttat | gggtagccat | 10620 |
| tgattgcctc | ctttgcaggc | agttggtggt | taggcgctgg | cggggtcact | accccccgcc | 10680 |
| tgcgccgctc | tgagttcttc | caggcactcg | cgcagcgcct | cgtattcgtc | gtcggtcagc | 10740 |
| cagaacttgc | gctgacgcat | cccttttggcc | ttcatgcgct | cggcatatcg | cgcttggcgt | 10800 |
| acagcgtcag | ggctggccag | caggtcgccg | gtctgcttgt | ccttttggtc | tttcatatca | 10860 |
| gtcaccgaga | aacttgccgg | ggccgaaagg | cttgtcttcg | cggaacaagg | acaaggtgca | 10920 |
| gccgtcaagg | ttaaggctgg | ccatatcagc | gactgaaaag | cggccagcct | cggccttgtt | 10980 |
| tgacgtataa | ccaaagccac | cgggcaacca | atagcccttg | tcactttga | tcaggtagac | 11040 |
| cgaccctgaa | gcgcttttt | cgtattccat | aaaacccct | tctgtgcgtg | agtactcata | 11100 |
| gtataacagg | cgtgagtacc | aacgcaagca | ctacatgctg | aaatctggcc | cgcccctgtc | 11160 |
| catgcctcgc | tggcggggtg | ccggtgcccg | tgccagctcg | gcccgcgcaa | gctggacgct | 11220 |
| gggcagaccc | atgaccttgc | tgacggtgcg | ctcgatgtaa | tccgcttcgt | ggccgggctt | 11280 |
| gcgctctgcc | agcgctgggc | tggcctcggc | catggccttg | ccgatttcct | cggcactgcg | 11340 |
| gccccggctg | gccagcttct | gcggcgat | aaagtcgcac | ttgctgaggt | catcaccgaa | 11400 |
| gcgcttgacc | agcccggcca | tctcgctgcg | gtactcgtcc | agcgccgtgc | gccggtggcg | 11460 |
| gctaagctgc | cgctcgggca | gttcgaggct | ggccagcctg | cgggccttct | cctgctgccg | 11520 |
| ctgggcctgc | tcgatctgct | ggccagcctg | ctgcaccagc | gccgggccag | cggtggcggt | 11580 |
| cttgcccttg | gattcacgca | gcagcaccca | cggctgataa | ccggcgcggg | tggtgtgctt | 11640 |
| gtccttgcgg | ttggtgaagc | ccgccaagcg | gccatagtgg | cggctgtcgg | cgctggccgg | 11700 |
| gtcggcgtcg | tactcgctgg | ccagcgtccg | ggcaatctgc | cccgaagtt | caccgcctgc | 11760 |
| ggcgtcggcc | accttgaccc | atgcctgata | gttcttcggg | ctggtttcca | ctaccagggc | 11820 |

-continued

```
aggctcccgg ccctcggctt tcatgtcatc caggtcaaac tcgctgaggt cgtccaccag    11880
caccagacca tgccgctcct gctcggcggg cctgatatac acgtcattgc cctgggcatt    11940
catccgcttg agccatggcg tgttctggag cacttcggcg gctgaccatt cccggttcat    12000
catctggccg gtggtggcgt ccctgacgcc gatatcgaag cgctcacagc ccatggcctt    12060
gagctgtcgg cctatggcct gcaaagtcct gtcgttcttc atcgggccac caagcgcagc    12120
cagatcgagc cgtcctcggt tgtcagtggc gtcaggtcga gcaagagcaa cgatgcgatc    12180
agcagcacca ccgtaggcat catggaagcc agcatcacgg ttagccatag cttccagtgc    12240 caccccccgcg acgcgctccg ggcgctctgc gcggcgctgc tcacctcggc ggctacctcc    12300
cgcaactctt tggccagctc cacccatgcc gcccctgtct ggcgctgggc tttcagccac    12360
tccgccgcct gcgcctcgct ggcctgctgg gtctggctca tgacctgccg ggcttcgtcg    12420
gccagtgtcg ccatgctctg ggccagcggt tcgatctgct ccgctaactc gttgatgcct    12480
ctggatttct tcactctgtc gattgcgttc atggtctatt gcctcccggt attcctgtaa    12540
gtcgatgatc tgggcgttgg cggtgtcgat gttcagggcc acgtctgccc ggtcggtgcg    12600
gatgccccgg ccttccatct ccaccacgtt cggcccagg tgaacaccgg gcaggcgctc    12660
gatgccctgc gcctcaagtg ttctgtggtc aatgcgggcg tcgtggccag cccgctctaa    12720
tgcccggttg gcatggtcgg cccatgcctc gcgggtctgc tcaagccatg ccttgggctt    12780
gagcgcttcg gtcttctgtg ccccgccctt ctccgggtc ttgccgttgt accgcttgaa    12840
ccactgagcg gcgggccgct cgatgccgtc attgatccgc tcggagatca tcaggtggca    12900
gtgcgggttc tcgccgccac cggcatggat ggccagcgta tacggcaggc gctcggcacc    12960
ggtcaggtgc tgggcgaact cggacgccag cgccttctgc tggtcgaggg tcagctcgac    13020
cggcagggca aattcgacct ccttgaacag ccgcccattg gcgcgttcat acaggtcggc    13080
agcatcccag tagtcggcgg gccgctcgac gaactccggc atgtgcccgg attcggcgtg    13140
caagacttca tccatgtcgc gggcatactt gccttcgcgc tggatgtagt cggccttggc    13200
cctggccgat tggccgcccg acctgctgcc ggttttcgcc gtaaggtgat aaatcgccat    13260
gctgcctcgc tgttgctttt gcttttcggc tccatgcaat ggccctcgga gagcgcaccg    13320
cccgaagggt ggccgttagg ccagtttctc gaagagaaac cggtaagtgc gccctcccct    13380
acaaagtagg gtcgggattg ccgccgctgt gcctccatga tagcctacga gacagcacat    13440
taacaatggg gtgtcaagat ggttaagggg agcaacaagg cggcggatcg gctggccaag    13500
ctcgaagaac aacgagcgcg aatcaatgcc gaaattcagc gggtgcgggc aagggaacag    13560
cagcaagagc gcaagaacga acaaggcgc aaggtgctgg tgggggccat gattttggcc    13620
aaggtgaaca gcagcgagtg gccggaggat cggctcatgg cggcaatgga tgcgtacctt    13680
gaacgcgacc acgaccgcgc cttgttcggt ctgccgccac gccagaagga tgagccgggc    13740
tgaatgatcg accgagacag gccctgcggg gctgcacacg cgcccccacc cttcgggtag    13800
ggggaaaggc cgctaaagcg gctaaaagcg ctccagcgta tttctgcggg gtttggtgtg    13860
gggtttagcg ggctttgccc gccttttccc ctgccgcgca gcggtggggc ggtgtgtagc    13920
ctagcgcagc gaatagacca gctatccggc ctctggccgg gcatattggg caagggcagc    13980
agcgccccac aagggcgctg ataaccgcgc ctagtggatt attcttagat aatcatggat    14040 ggattttttcc aacaccccgc cagccccgc ccctgctggg tttgcaggtt tggggggcgtg    14100 acagttattg caggggttcg tgacagttat tgcaggggg cgtgacagtt attgcagggg    14160
ttcgtgacag ttagtacggg agtgacgggc actggctggc aatgtctagc aacggcaggc    14220
```

```
atttcggctg agggtaaaag aactttccgc taagcgatag actgtatgta aacacagtat    14280
tgcaaggacg cggaacatgc ctcatgtggc ggccaggacg gccagccggg atcgggatac    14340
tggtcgttac cagagccacc gacccgagca aaccctnctc tatcagatcg ttgacgagta    14400
ttacccggca ttcgctgcgc ttatggcaga gcagggaaag gaattgccgg gctatgtgca    14460
acgggaattt gaagaatttc tccaatgcgg gcggctggag catggctttc tacgggttcg    14520
ctgcgagtct tgccacgccg agcacctggt cgctttcagc tgtaagcgtc gcggtttctg    14580
cccgagctgt ggggcgcggc ggatggccga aagtgccgcc ttgctggttg atgaagtact    14640
gcctgaacaa cccatgcgtc agtgggtgtt gagcttcccg tttcagctgc gtttcctgtt    14700
tggggtcgtt tgcgggaagg ggcggaatcc tacgctaagg cttttggccag cgatattctc    14760 cggtgagatt gatgtgttcc caggggatag agaagtcgc ttgatatcta gtatgacgtc    14820
tgtcgcacct gcttgatcgc ggcccaaggg ttggtttgcg cattcacagt tctccgcaag    14880
aattgattgg ctccaattct tggagtggtg aatccgttag cgaggtgccg ccggcttcca    14940
ttcaggtcga ggtggcccgg ctccatgcac cgcgacgcaa cgcggggagg cagacaaggt    15000
atagggcggc gcctacaatc catgccaacc cgttccatgt gctcgccgag gcggcataaa    15060
tcgccgtgac gatcagcggt ccagtgatcg aagttaggct ggtaagagcc gcgagcgatc    15120
cttgaagctg tccctgatgg tcgtcatcta cctgcctgga cagcatggcc tgcaacgcgg    15180
gcatcccgat gccgcggaa gcgagaagaa tcataatggg gaaggccatc cagcctcgcg    15240
tcgcgaacgc cagcaagacg tagcccagcg cgtcggccgc catgccggcg ataatggcct    15300
gcttctcgcc gaaacgtttg gtggcgggac cagtgacgaa ggcttgagcg agggcgtgca    15360
agattccgaa taccgcaagc gacaggccga tcatcgtcgc gctccagcga aagcggtcct    15420
cgccgaaaat gacccagagc gctgccggca cctgtcctac gagttgcatg ataaagaaga    15480
cagtcataag tgcggcgacg atagtcatgc cccgcgccca ccggaaggag ctgactgggt    15540
tgaaggctct caagggcatc ggtcgacgct ctcccttatg cgactcctgc attaggaagc    15600
agcccagtag taggttgagg ccgttgagca ccgccgccgc aaggaatggt gcatgcaagg    15660
agatggcgcc caacagtccc ccggccacgg ggcctgccac catacccacg ccgaaacaag    15720
cgctcatgag cccgaagtgg cgagcccgat cttccccatc ggtgatgtcg gcgatatagg    15780
cgccagcaac cgcacctgtg gcgccggtga tgccggccac gatgcgtccg gcgtagagga    15840
tccacaggac gggtgtggtc gccatgatcg cgtagtcgat agtggctcca agtagcgaag    15900
cgagcaggac tgggcggcgg ccaaagcggt cggacagtgc tccgagaacg ggtgcgcata    15960
gaaattgcat caacgcatat agcgctagca gcacgccata gtgactggcg atgctgtcgg    16020
aatggacgat atcccgcaag aggcccggca gtaccggcat aaccaagcct atgcctacag    16080
catccagggt gacggtgccg aggatgacga tgagcgcatt gttagatttc atacacggtg    16140
cctgactgcg ttagcaattt aactgtgata aactaccgca ttaaagctta tcgatgataa    16200
gctgtcaaac atga                                                     16214
```

<210> SEQ ID NO 10
<211> LENGTH: 696
<212> TYPE: PRT
<213> ORGANISM: Artificial sequence
<220> FEATURE:
<223> OTHER INFORMATION: artificial sequence
<220> FEATURE:
<221> NAME/KEY: MISC_FEATURE
<222> LOCATION: (5)..(696)

<223> OTHER INFORMATION: Xaa = any amino acid residue

<400> SEQUENCE: 10

```
Met Trp Arg Arg Xaa Ile Tyr His Pro Xaa Xaa Asn Tyr Ala Leu Arg
1               5                   10                  15

Gln Thr Leu Val Leu Cys Leu Pro Val Ala Xaa Gly Xaa Xaa Xaa Gly
            20                  25                  30

Xaa Leu Xaa Xaa Gly Leu Leu Phe Ser Leu Val Pro Ala Cys Cys Asn
        35                  40                  45

Ile Ala Gly Leu Asp Thr Pro His Lys Arg Phe Phe Lys Xaa Leu Ile
50                  55                  60

Ile Gly Xaa Ser Leu Phe Ala Xaa Xaa Ser Leu Xaa Xaa Gln Xaa Leu
65                  70                  75                  80

Leu Xaa Xaa Xaa Xaa Pro Leu Pro Xaa Xaa Leu Xaa Xaa Leu Xaa Leu
                85                  90                  95

Xaa Leu Gly Val Thr Xaa Glu Xaa Xaa Pro Leu His Ala Xaa Leu Leu
            100                 105                 110

Pro Xaa Xaa Leu Xaa Ala Ala Ile Phe Thr Leu Ser Leu Xaa Gly Xaa
        115                 120                 125

Met Pro Xaa Xaa Xaa Pro Xaa Leu Xaa Tyr Xaa Xaa Gly Thr Leu Trp
130                 135                 140

Tyr Gly Xaa Phe Asn Trp Phe Trp Phe Trp Xaa Trp Xaa Glu Gln Pro
145                 150                 155                 160

Xaa Arg Glu Ser Leu Ser Leu Xaa Tyr Arg Glu Leu Ala Xaa Tyr Cys
            165                 170                 175

Xaa Ala Lys Tyr Ser Leu Leu Thr Gln Xaa Xaa Asp Pro Glu Lys Ala
        180                 185                 190

Leu Pro Pro Leu Leu Xaa Arg Gln Gln Lys Ala Xaa Asp Leu Ile Xaa
    195                 200                 205

Xaa Cys Tyr Gln Gln Met His Met Leu Ser Ala Xaa Xaa Xaa Xaa Xaa
210                 215                 220

Xaa Lys Arg Xaa Xaa Arg Xaa Phe Gln Xaa Ala Xaa Asp Leu Gln Glu
225                 230                 235                 240

His Ile Ser Val Ser Leu His Gln Pro Glu Val Gln Lys Leu Val
            245                 250                 255

Glu Xaa Ser His Ala Glu Xaa Val Ile Arg Trp Asn Ala Xaa Thr Xaa
            260                 265                 270

Xaa Ala Arg Leu Arg Xaa Leu Ala Asp Asp Ile Leu Tyr His Xaa Leu
        275                 280                 285

Xaa Xaa Arg Phe Xaa Met Xaa Lys Gln Xaa Gly Ala Leu Glu Lys Ile
    290                 295                 300

Ala Xaa Gln His Pro Xaa Asn Pro Val Gly Xaa Phe Cys Xaa Xaa His
305                 310                 315                 320

Phe Ser Arg Ile Ala Arg Val Leu Arg Thr Gln Xaa Pro Leu Tyr Xaa
            325                 330                 335

Arg Asp Leu Xaa Ala Asp Xaa Gln Arg Arg Xaa Pro Leu Leu Pro Ala
        340                 345                 350

Leu Xaa Xaa Tyr Xaa Ser Leu Xaa Ser Xaa Ala Leu Arg Xaa Ala Gly
    355                 360                 365

Arg Xaa Ser Val Met Xaa Xaa Xaa Ser Xaa Xaa Xaa Xaa Xaa Xaa Xaa
370                 375                 380

Xaa Xaa Pro Lys Xaa Tyr Trp Ile Leu Met Thr Xaa Xaa Xaa Val Xaa
385                 390                 395                 400
```

```
Gln Xaa Xaa Tyr Xaa Ala Thr Arg Xaa Arg Ile Xaa Xaa Arg Xaa Xaa
            405                 410                 415

Gly Thr Xaa Xaa Gly Leu Xaa Ile Ala Xaa Xaa Xaa Leu Xaa Xaa Xaa
        420                 425                 430

Xaa Pro Glu Xaa Xaa Leu Xaa Xaa Met Leu Xaa Xaa Thr Xaa Xaa
        435                 440                 445

Ser Tyr Xaa Xaa Xaa Arg Xaa Xaa Tyr Gly Trp Xaa Xaa Val Gly Phe
    450                 455                 460

Thr Xaa Thr Ala Val Tyr Thr Xaa Gln Leu Leu Xaa Leu Asn Gly Xaa
465                 470                 475                 480

Gln Xaa Xaa Xaa Pro Arg Leu Xaa Asp Thr Xaa Xaa Gly Cys Leu Ile
                485                 490                 495

Ala Phe Gly Gly Xaa Xaa Trp Leu Trp Pro Gln Trp Gln Ser Xaa Leu
                500                 505                 510

Leu Arg Xaa Asn Ala His Asp Ala Leu Glu Ala Xaa Gln Xaa Ala Xaa
        515                 520                 525

Arg Xaa Xaa Leu Xaa Xaa Xaa Xaa Xaa Xaa Xaa Leu Ala Xaa Gln
    530                 535                 540

Arg Xaa Xaa Val Asn Gln Ala His Asn Xaa Xaa Xaa Asn Ser Leu Asn
545                 550                 555                 560

Gln Ala Met Gln Glu Pro Xaa Phe Asn Xaa Xaa Tyr Leu Xaa Asp Met
                565                 570                 575

Xaa Leu Trp Val Thr His Xaa Gln Phe Ile Val Glu His Ile Asn Ala
        580                 585                 590

Met Thr Xaa Leu Ala Arg Glu His Xaa Xaa Leu Xaa Pro Xaa Leu Ala
        595                 600                 605

Xaa Xaa Tyr Leu Xaa Xaa Cys Glu Ile Ala Xaa Gln Arg Cys Gln Gln
610                 615                 620

Arg Leu Glu Tyr Asp Xaa Pro Gly Xaa Ser Xaa Xaa Xaa Xaa Xaa
625                 630                 635                 640

Xaa Xaa Xaa Xaa Xaa Xaa Xaa Xaa Xaa Xaa Xaa Xaa Xaa Thr Leu Glu
            645                 650                 655

Gln His Xaa Xaa Arg Xaa Xaa Xaa His Leu Xaa Xaa Met His Thr Ile
            660                 665                 670

Ser Ser Xaa Ala Trp Xaa Gln Arg Pro His His Gly Xaa Trp Leu Xaa
        675                 680                 685

Xaa Xaa Leu Arg Xaa Xaa Lys Xaa
    690                 695

<210> SEQ ID NO 11
<211> LENGTH: 696
<212> TYPE: PRT
<213> ORGANISM: artificial sequence
<220> FEATURE:
<221> NAME/KEY: MISC_FEATURE
<222> LOCATION: (10)..(696)
<223> OTHER INFORMATION:
<220> FEATURE:
<221> NAME/KEY: MISC_FEATURE
<222> LOCATION: (10)..(696)
<223> OTHER INFORMATION: Xaa = any amino acid residue

<400> SEQUENCE: 11

Met Trp Arg Arg Leu Ile Tyr His Pro Xaa Ile Asn Tyr Ala Leu Arg
1               5                   10                  15

Gln Thr Leu Val Leu Cys Leu Pro Val Ala Val Gly Leu Xaa Leu Gly
            20                  25                  30
```

```
Xaa Leu Xaa Phe Gly Leu Leu Phe Ser Leu Val Pro Ala Cys Cys Asn
         35                  40                  45

Ile Ala Gly Leu Asp Thr Pro His Lys Arg Phe Phe Lys Arg Leu Ile
 50                  55                  60

Ile Gly Ala Ser Leu Phe Ala Xaa Cys Ser Leu Xaa Thr Gln Leu Leu
 65                  70                  75                  80

Leu Ala Xaa Xaa Xaa Pro Leu Pro Xaa Xaa Leu Thr Gly Leu Thr Leu
                 85                  90                  95

Val Leu Gly Val Thr Ala Glu Xaa Xaa Pro Leu His Ala Xaa Leu Leu
             100                 105                 110

Pro Ala Ser Leu Xaa Ala Ala Ile Phe Thr Leu Ser Leu Ala Gly Tyr
             115                 120                 125

Met Pro Val Trp Glu Pro Leu Leu Ile Tyr Ala Leu Gly Thr Leu Trp
             130                 135                 140

Tyr Gly Xaa Phe Asn Trp Phe Trp Phe Trp Xaa Trp Arg Glu Gln Pro
145                 150                 155                 160

Leu Arg Glu Ser Leu Ser Leu Leu Tyr Arg Glu Leu Ala Asp Tyr Cys
                165                 170                 175

Glu Ala Lys Tyr Ser Leu Leu Thr Gln His Xaa Asp Pro Glu Lys Ala
            180                 185                 190

Leu Pro Pro Leu Leu Xaa Arg Gln Gln Lys Ala Val Asp Leu Ile Thr
            195                 200                 205

Gln Cys Tyr Gln Gln Met His Met Leu Ser Ala Xaa Asn Asn Xaa Asp
        210                 215                 220

Tyr Lys Arg Xaa Leu Arg Xaa Phe Gln Glu Ala Xaa Asp Leu Gln Glu
225                 230                 235                 240

His Ile Ser Val Ser Leu His Gln Pro Glu Glu Val Gln Lys Leu Val
                245                 250                 255

Glu Arg Ser His Ala Glu Glu Val Ile Arg Trp Asn Ala Gln Thr Val
            260                 265                 270

Ala Ala Arg Leu Arg Val Leu Ala Asp Asp Ile Leu Tyr His Arg Leu
        275                 280                 285

Pro Thr Arg Phe Xaa Met Glu Lys Gln Ile Gly Ala Leu Glu Lys Ile
        290                 295                 300

Ala Xaa Gln His Pro Xaa Asn Pro Val Gly Gln Phe Cys Tyr Trp His
305                 310                 315                 320

Phe Ser Arg Ile Ala Arg Val Leu Arg Thr Gln Xaa Pro Leu Tyr Ala
                325                 330                 335

Arg Asp Leu Xaa Ala Asp Lys Gln Arg Arg Xaa Pro Leu Leu Pro Ala
            340                 345                 350

Leu Lys Xaa Tyr Xaa Ser Leu Lys Ser Pro Ala Leu Arg Asn Ala Gly
        355                 360                 365

Arg Xaa Ser Val Met Xaa Ser Val Ala Ser Leu Met Gly Xaa Ala Leu
    370                 375                 380

His Leu Pro Lys Xaa Tyr Trp Ile Leu Met Thr Val Leu Xaa Val Thr
385                 390                 395                 400

Gln Asn Gly Tyr Gly Ala Thr Arg Xaa Arg Ile Xaa Xaa Arg Ser Val
                405                 410                 415

Gly Thr Xaa Val Gly Leu Xaa Ile Ala Gly Val Xaa Leu His Xaa Xaa
            420                 425                 430

Ile Pro Glu Xaa Xaa Thr Leu Xaa Leu Met Leu Xaa Xaa Thr Leu Ala
        435                 440                 445

Ser Tyr Leu Ile Xaa Arg Lys Asn Tyr Gly Trp Ala Thr Val Gly Phe
```

```
                450             455             460
Thr Xaa Thr Ala Val Tyr Thr Xaa Gln Leu Leu Xaa Leu Asn Gly Glu
465                 470                 475                 480

Gln Xaa Ile Xaa Pro Arg Leu Ile Asp Thr Xaa Ile Gly Cys Leu Ile
            485                 490                 495

Ala Phe Gly Gly Xaa Val Trp Leu Trp Pro Gln Trp Gln Ser Gly Leu
                500                 505                 510

Leu Arg Lys Asn Ala His Asp Ala Leu Glu Ala Xaa Gln Glu Ala Ile
            515                 520                 525

Arg Leu Ile Leu Ser Xaa Asp Pro Gln Xaa Thr Pro Leu Ala Xaa Gln
530                 535                 540

Arg Met Arg Val Asn Gln Ala His Asn Thr Leu Xaa Asn Ser Leu Asn
545                 550                 555                 560

Gln Ala Met Gln Glu Pro Xaa Phe Asn Xaa His Tyr Leu Xaa Asp Met
                565                 570                 575

Lys Leu Trp Val Thr His Ser Gln Phe Ile Val Glu His Ile Asn Ala
            580                 585                 590

Met Thr Thr Leu Ala Arg Glu His Xaa Xaa Leu Xaa Pro Xaa Leu Ala
            595                 600                 605

Gln Xaa Tyr Leu Xaa Ser Cys Glu Ile Ala Ile Gln Arg Cys Gln Gln
610                 615                 620

Arg Leu Glu Tyr Asp Xaa Pro Gly Xaa Ser Gly Asp Xaa Asn Ile Xaa
625                 630                 635                 640

Xaa Xaa Pro Xaa Met Xaa Pro Xaa Glu Gly Xaa Xaa Thr Leu Glu
                645                 650                 655

Gln His Leu Gln Arg Xaa Ile Gly His Leu Asn Thr Met His Thr Ile
            660                 665                 670

Ser Ser Met Ala Trp Arg Gln Arg Pro His His Gly Ile Trp Leu Ser
            675                 680                 685

Xaa Xaa Leu Arg Asp Xaa Lys Xaa
            690                 695

<210> SEQ ID NO 12
<211> LENGTH: 696
<212> TYPE: PRT
<213> ORGANISM: artificial sequence
<220> FEATURE:
<221> NAME/KEY: MISC_FEATURE
<222> LOCATION: (10)..(696)
<223> OTHER INFORMATION: Xaa = any amino acid residue

<400> SEQUENCE: 12

Met Trp Arg Arg Leu Ile Tyr His Pro Xaa Ile Asn Tyr Ala Leu Arg
1               5                   10                  15

Gln Thr Leu Val Leu Cys Leu Pro Val Ala Val Gly Leu Xaa Xaa Gly
            20                  25                  30

Xaa Leu Xaa Xaa Gly Leu Leu Phe Ser Leu Val Pro Ala Cys Cys Asn
        35                  40                  45

Ile Ala Gly Leu Asp Thr Pro His Lys Arg Phe Phe Lys Arg Leu Ile
50                  55                  60

Ile Gly Ala Ser Leu Phe Ala Xaa Cys Ser Leu Xaa Thr Gln Leu Leu
65                  70                  75                  80

Leu Ala Xaa Xaa Xaa Pro Leu Pro Xaa Xaa Leu Thr Gly Leu Thr Leu
                85                  90                  95

Val Leu Gly Val Thr Ala Glu Xaa Xaa Pro Leu His Ala Xaa Leu Leu
            100                 105                 110
```

```
Pro Ala Ser Leu Xaa Ala Ala Ile Phe Thr Leu Ser Leu Ala Gly Tyr
            115                 120                 125
Met Pro Val Trp Glu Pro Leu Leu Ile Tyr Ala Leu Gly Thr Leu Trp
            130                 135                 140
Tyr Gly Xaa Phe Asn Trp Phe Trp Phe Trp Xaa Trp Arg Glu Gln Pro
145                 150                 155                 160
Leu Arg Glu Ser Leu Ser Leu Leu Tyr Arg Glu Leu Ala Asp Tyr Cys
            165                 170                 175
Glu Ala Lys Tyr Ser Leu Leu Thr Gln His Xaa Asp Pro Glu Lys Ala
            180                 185                 190
Leu Pro Pro Leu Leu Xaa Arg Gln Gln Lys Ala Val Asp Leu Ile Thr
            195                 200                 205
Gln Cys Tyr Gln Gln Met His Met Leu Ser Ala Xaa Asn Asn Xaa Asp
            210                 215                 220
Tyr Lys Arg Xaa Leu Arg Xaa Phe Gln Glu Ala Xaa Asp Leu Gln Glu
225                 230                 235                 240
His Ile Ser Val Ser Leu His Gln Pro Glu Glu Val Gln Lys Leu Val
            245                 250                 255
Glu Arg Ser His Ala Glu Glu Val Ile Arg Trp Asn Ala Gln Thr Val
            260                 265                 270
Ala Ala Arg Leu Arg Val Leu Ala Asp Asp Ile Leu Tyr His Arg Leu
            275                 280                 285
Pro Thr Arg Phe Xaa Met Glu Lys Gln Ile Gly Ala Leu Glu Lys Ile
            290                 295                 300
Ala Xaa Gln His Pro Xaa Asn Pro Val Gly Gln Phe Cys Tyr Trp His
305                 310                 315                 320
Phe Ser Arg Ile Ala Arg Val Leu Arg Thr Gln Xaa Pro Leu Tyr Ala
            325                 330                 335
Arg Asp Leu Xaa Ala Asp Lys Gln Arg Arg Xaa Pro Leu Leu Pro Ala
            340                 345                 350
Leu Lys Xaa Tyr Xaa Ser Leu Lys Ser Pro Ala Leu Arg Asn Ala Gly
            355                 360                 365
Arg Xaa Ser Val Met Xaa Ser Xaa Ala Ser Leu Met Gly Xaa Ala Leu
            370                 375                 380
His Leu Pro Lys Xaa Tyr Trp Ile Leu Met Thr Val Leu Xaa Val Thr
385                 390                 395                 400
Gln Asn Gly Tyr Gly Ala Thr Arg Xaa Arg Ile Xaa Xaa Arg Ser Val
            405                 410                 415
Gly Thr Xaa Val Gly Leu Xaa Ile Ala Gly Val Xaa Leu His Xaa Xaa
            420                 425                 430
Ile Pro Glu Gly Xaa Thr Leu Xaa Xaa Met Leu Xaa Xaa Thr Leu Ala
            435                 440                 445
Ser Tyr Leu Ile Xaa Arg Lys Asn Tyr Gly Trp Ala Thr Val Gly Phe
            450                 455                 460
Thr Xaa Thr Ala Val Tyr Thr Xaa Gln Leu Leu Xaa Leu Asn Gly Glu
465                 470                 475                 480
Gln Tyr Xaa Xaa Pro Arg Leu Ile Asp Thr Xaa Ile Gly Cys Leu Ile
            485                 490                 495
Ala Phe Gly Gly Xaa Val Trp Leu Trp Pro Gln Trp Ser Gly Leu
            500                 505                 510
Leu Arg Lys Asn Ala His Asp Ala Leu Glu Ala Xaa Gln Glu Ala Ile
            515                 520                 525
```

-continued

```
Arg Leu Ile Leu Ser Xaa Asp Pro Gln Xaa Thr Pro Leu Ala Xaa Gln
        530             535             540

Arg Met Arg Val Asn Gln Ala His Asn Thr Leu Xaa Asn Ser Leu Asn
545                 550                 555                 560

Gln Ala Met Gln Glu Pro Xaa Phe Asn Xaa His Tyr Leu Xaa Asp Met
            565             570                 575

Lys Leu Trp Val Thr His Ser Gln Phe Ile Val Glu His Ile Asn Ala
            580             585                 590

Met Thr Thr Leu Ala Arg Glu His Xaa Xaa Leu Xaa Pro Xaa Leu Ala
        595             600             605

Gln Xaa Tyr Leu Xaa Ser Cys Glu Ile Ala Ile Gln Arg Cys Gln Gln
    610             615             620

Arg Leu Glu Tyr Asp Xaa Pro Gly Xaa Ser Gly Asp Xaa Asn Ile Xaa
625             630             635                 640

Xaa Ala Pro Xaa Met Xaa Pro Xaa Xaa Gly Ala Ala Gly Thr Leu Glu
            645             650                 655

Gln His Leu Gln Arg Xaa Ile Gly His Leu Asn Thr Met His Thr Ile
            660             665                 670

Ser Ser Met Ala Trp Arg Gln Arg Pro His His Gly Ile Trp Leu Ser
        675             680             685

Xaa Xaa Leu Arg Asp Xaa Lys Xaa
    690             695
```